US012773191B2

(12) United States Patent
Moyer et al.

(10) Patent No.: US 12,773,191 B2
(45) **Date of Patent: *Oct. 27, 2026**

(54) INGESTIBLE DEVICE WITH PROPULSION AND IMAGING CAPABILITIES

(71) Applicant: Endiatx, Inc., Hayward, CA (US)

(72) Inventors: Daniel V. Moyer, Redwood City, CA (US); Torrey P. Smith, Redwood City, CA (US); James G. Erd, Newark, CA (US); Daniel A. Luebke, San Mateo, CA (US); Benjamin J. Bonnes, Oakland, CA (US); Marcus X. Luebke, San Mateo, CA (US); Rachel N. New, Palo Alto, CA (US); William J. Buxton, Palo Alto, CA (US)

(73) Assignee: Endiatx, Inc., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/032,401

(22) Filed: Jan. 20, 2025

(65) Prior Publication Data

US 2025/0302456 A1 Oct. 2, 2025

Related U.S. Application Data

(63) Continuation of application No. 18/184,157, filed on Mar. 15, 2023, now Pat. No. 12,201,279, which is a (Continued)

(51) Int. Cl.

*A61B 1/04* (2006.01)
*A61B 1/00* (2006.01)

(Continued)

(52) U.S. Cl.

CPC .......... *A61B 10/04* (2013.01); *A61B 1/00006* (2013.01); *A61B 1/00009* (2013.01);

(Continued)

(58) Field of Classification Search

CPC ......... H04N 5/23203; H04N 5/232411; H04N 5/23299; H04N 5/40; H04N 17/002;

(Continued)

(56) References Cited

U.S. PATENT DOCUMENTS 5,427,144 A 6/1995 Teets et al.
6,073,569 A 6/2000 Motsenbocker et al.

(Continued)

FOREIGN PATENT DOCUMENTS

CN 101502410 A 8/2009
CN 106462756 A 2/2017

(Continued)

OTHER PUBLICATIONS

Tortora, Giuseppe et al., Propeller-based wireless device for active capsular endoscopy in the gastric district, Minimally Invasive Therapy & Technologies, Dec. 31, 2009, vol. 8, Issue 5, Informa Healthcare.

*Primary Examiner* — Howard D Brown, Jr.

(74) *Attorney, Agent, or Firm* — Ashurst Perkins Coie US LLP

(57) ABSTRACT

An ingestible device comprising a capsule, a camera, an antenna, and a propulsion component id disclosed. The camera can capture images of various in vivo environments as the ingestible device traverses the gastrointestinal tract, and these images can be wirelessly transmitted to an electronic device located outside of the living body. The images may be transmitted to the electronic device for review by an operator responsible for controlling the ingestible device.

20 Claims, 16 Drawing Sheets

Related U.S. Application Data continuation of application No. 16/915,735, filed on Jun. 29, 2020, now Pat. No. 11,622,754.

(60) Provisional application No. 62/868,109, filed on Jun. 28, 2019.

(51) Int. Cl.

| | |
|---|---|
| ***A61B 1/045*** | (2006.01) |
| ***A61B 1/06*** | (2006.01) |
| ***A61B 1/31*** | (2006.01) |
| ***A61B 10/04*** | (2006.01) |
| ***A61B 17/34*** | (2006.01) |
| ***H01Q 7/00*** | (2006.01) |
| ***H01Q 9/00*** | (2006.01) |
| ***H04B 1/713*** | (2011.01) |
| ***H04N 5/40*** | (2006.01) |
| ***H04N 17/00*** | (2006.01) |
| ***H04N 23/54*** | (2023.01) |
| ***H04N 23/56*** | (2023.01) |
| ***H04N 23/65*** | (2023.01) |
| ***H04N 23/66*** | (2023.01) |
| ***H04N 23/695*** | (2023.01) |
| ***H04W 76/14*** | (2018.01) |
| *A61B 10/02* | (2006.01) |
| *H04N 23/50* | (2023.01) |

(52) U.S. Cl.

CPC ...... *A61B 1/00016* (2013.01); *A61B 1/00032* (2013.01); *A61B 1/00036* (2013.01); *A61B 1/0011* (2013.01); *A61B 1/00156* (2013.01); *A61B 1/0016* (2013.01); *A61B 1/041* (2013.01); *A61B 1/045* (2013.01); *A61B 1/0661* (2013.01); *A61B 1/31* (2013.01); *A61B 17/3478* (2013.01); *A61B 17/3496* (2013.01); *H01Q 7/00* (2013.01); *H01Q 9/00* (2013.01); *H04B 1/713* (2013.01); *H04N 5/40* (2013.01); *H04N 17/002* (2013.01); *H04N 23/54* (2023.01); *H04N 23/56* (2023.01); *H04N 23/651* (2023.01); *H04N 23/66* (2023.01); *H04N 23/695* (2023.01); *H04W 76/14* (2018.02); *A61B 1/06* (2013.01); *A61B 2010/0208* (2013.01); *A61B 2010/045* (2013.01); *H04N 23/555* (2023.01)

(58) Field of Classification Search

CPC ........... H04N 2005/2255; H04W 76/14; A61B 2010/0208; A61B 2010/045; A61B 5/073; A61B 2562/162; A61B 1/0002

See application file for complete search history.

(56) References Cited

U.S. PATENT DOCUMENTS

| | | | | |
|---|---|---|---|---|
| 6,240,312 | B1 * | 5/2001 | Alfano | A61B 5/0031 128/903 |
| 7,643,865 | B2 * | 1/2010 | Iddan | A61B 1/00156 600/302 |
| 7,647,090 | B1 * | 1/2010 | Frisch | A61B 5/073 600/109 |
| 8,439,851 | B2 * | 5/2013 | Chiba | A61B 5/6861 600/593 |
| 8,529,436 | B2 * | 9/2013 | Jung | A61B 1/041 600/117 |
| 10,172,598 | B2 | 1/2019 | Amoako-Tuffour et al. | |
| 2001/0035902 | A1 | 11/2001 | Iddan | |
| 2005/0049488 | A1 | 3/2005 | Homan | |
| 2005/0177069 | A1 | 8/2005 | Takizawa et al. | |
| 2008/0167523 | A1 * | 7/2008 | Uchiyama | A61B 5/073 600/114 |
| 2008/0188710 | A1 | 8/2008 | Segawa et al. | |
| 2009/0008499 | A1 | 1/2009 | Shaw | |
| 2009/0318761 | A1 | 12/2009 | Rabinovitz | |
| 2011/0282144 | A1 * | 11/2011 | Gettman | A61B 1/041 600/109 |
| 2015/0011829 | A1 * | 1/2015 | Wang | A61B 1/045 600/118 |
| 2015/0156879 | A1 | 6/2015 | Pouget et al. | |
| 2016/0141485 | A1 * | 5/2016 | Lee | A61B 1/041 310/317 |
| 2017/0119235 | A1 | 5/2017 | Hyde et al. | |
| 2017/0119278 | A1 * | 5/2017 | Hyde | A61B 5/11 |
| 2017/0360283 | A1 * | 12/2017 | Kimura | A61B 1/041 |
| 2018/0000502 | A1 | 1/2018 | Baym et al. | |
| 2018/0082101 | A1 | 3/2018 | Zhang et al. | |
| 2019/0008388 | A1 * | 1/2019 | Ando | G02B 21/16 |
| 2019/0116660 | A1 | 4/2019 | Morning-Smith et al. | |
| 2020/0352424 | A1 * | 11/2020 | Rentschler | A61B 1/31 |
| 2021/0015510 | A1 | 1/2021 | Peng | |
| 2021/0060296 | A1 | 3/2021 | Velis | |

FOREIGN PATENT DOCUMENTS

| | | | | |
|---|---|---|---|---|
| DE | 19960250 | A1 | 6/2001 | |
| JP | 2004533879 | A | 11/2004 | |
| JP | 2006297080 | A | 5/2009 | |
| JP | 2016506810 | A | 6/2018 | |
| WO | 2007010997 | A1 | 1/2007 | |
| WO | 2010093042 | A1 | 8/2012 | |
| WO | 2013168710 | A1 | 11/2013 | |
| WO | WO-2020100321 | A1 * | 5/2020 | A61B 1/041 |
| WO | WO-2020264524 | A1 * | 12/2020 | H04N 23/695 |

* cited by examiner

INGESTIBLE DEVICE WITH PROPULSION AND IMAGING CAPABILITIES

CROSS-REFERENCE TO RELATED APPLICATIONS

This application is a continuation of U.S. application Ser. No. 18/184,157, filed Mar. 15, 2023, which is a continuation of U.S. application Ser. No. 16/915,735, filed Jun. 29, 2020, now U.S. Pat. No. 11,622,754, issued on Apr. 11, 2023, which claims the benefit of U.S. Provisional Application No. 62/868,109, filed on Jun. 28, 2019, each of which is incorporated herein by reference in its entirety.

TECHNICAL FIELD

Various embodiments concern devices designed to generate images of biological structures located inside of a living body and then transmit the images to an electronic device located outside of the living body.

BACKGROUND

An endoscopy is a medical procedure during which structures within a living body are visually examined with a camera that is affixed to the end of a flexible tube. Alternatively, an optical fiber exposed near the end of the flexible tube may carry light reflected by the structures within the body to a camera located outside the living body. The flexible tube is used to position the camera or the optical fiber in a desired position. A medical professional can diagnose conditions that affect the living body by examining images generated by the camera. For example, during an upper endoscopy, the flexible tube is inserted through the mouth or nose so that the medical professional can examine the esophagus, stomach, or upper part of the small intestine (also referred to as the "duodenum"). During a lower endoscopy (also referred to as a "colonoscopy"), the flexible tube is inserted through the rectum so that the medical professional can examine the large intestine (also referred to as the "colon").

Advances have been made in the quality, reliability, and safety of endoscopies. For instance, improvements in camera resolution have allowed medical professionals to provide more informed (and thus more accurate) opinions. Endoscopies are invasive procedures, however, and therefore have several potential complications. Patients may suffer infection, unexpected reactions to sedation (including death), bleeding (e.g., due to the removal of tissue for testing as part of a biopsy test), or tearing of tissue due to the friction of advancing the flexible tube through tortuosity, especially in cancer patients where chemotherapy drugs have weakened the tissues of the gastrointestinal (GI) tract or in pediatric patients whose anatomy is more fragile and/or physically smaller.

Moreover, endoscopies can be time-consuming procedures that require expensive hospital resources. For example, a patient may be instructed to prepare for an endoscopy while at home, travel to a medical setting, and then remain in the medical setting until sufficient recovery has occurred. This experience can take 8-12 hours despite the endoscopy itself lasting only 15-30 minutes. Recovery time associated with sedation that is spent in a medical setting, such as a hospital or a clinic, may be a significant contributor to the overall cost of the procedure.

BRIEF DESCRIPTION OF THE DRAWINGS

Various features of the technology will become more apparent to those skilled in the art from a study of the Detailed Description in conjunction with the drawings. Embodiments of the technology are illustrated by way of example and not limitation in the drawings, in which like references may indicate similar elements.

DETAILED DESCRIPTION

Figure 1:
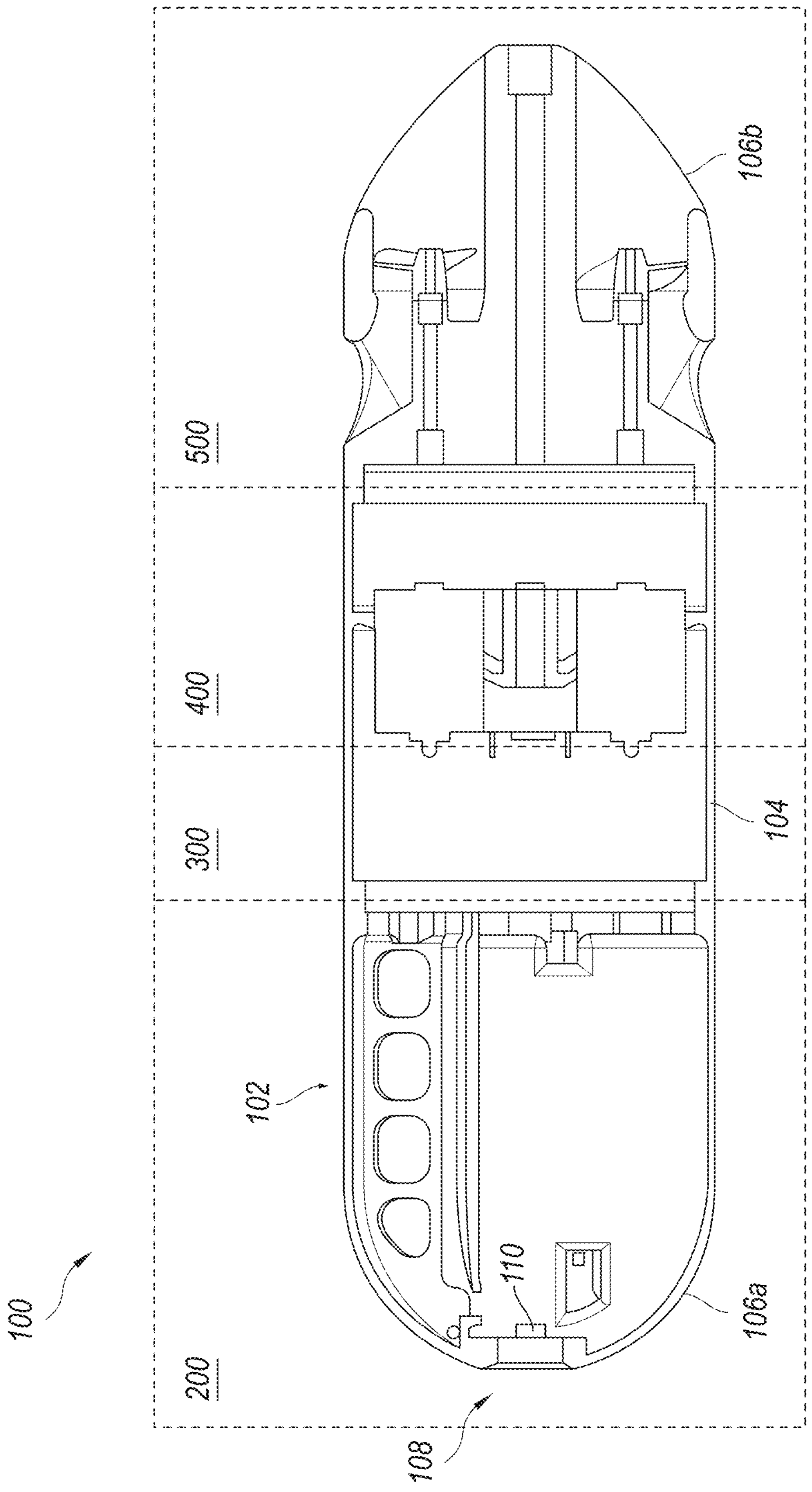
FIG. 1 includes a cross-sectional view of an example of a propulsive ingestible device designed to monitor in vivo environments as it travels through a living body, such as a human body or an animal body, under its own power.

Contemporary research has begun exploring how to monitor in vivo environments in a more effective manner. For example, several entities have developed cameras capable of capturing images of the digestive tract. Generally, these cameras are placed within vitamin-size capsules that can be swallowed by patients. The camera can generate hundreds or thousands of images as the capsule travels through the digestive tract, and these images can be wirelessly transmitted to an electronic device carried by the patient. This procedure is referred to as "capsule endoscopy."

Capsule endoscopy allows medical professionals to observe in vivo environments, such as the small intestine, that cannot easily be reached with conventional endoscopes. However, capsule endoscopy remains a relatively uncommon procedure. One reason for this is the lack of control over the camera following ingestion of the capsule. Areas of interest can be missed by the camera due to the orientation of the capsule as it naturally travels through the digestive tract. Another reason is that the devices used for capsule endoscopy can take several hours to reach the target anatomy and then several more hours to record imagery. Then, the patient may need to return to a medical setting (e.g., a hospital or clinic) to deliver the recorded imagery.

Introduced here, therefore, is a propulsive ingestible device (also referred to as a "pill" or a "pillbot") comprising a capsule (also referred to as an "enclosure"), a camera, an antenna, and one or more propulsion components and propulsion control elements. Because the ingestible device is designed to propel itself through a living body, the ingestible device may be referred to as a "propulsive device."

The camera can generate images as the ingestible device traverses the gastrointestinal tract. The camera may be designed to capture images at a variety of frame rates, for example 2, 6, or 15 frames per second (fps). In some embodiments, the camera may capture more than 15 fps. The frame rate may vary based on the speed at which the ingestible device is traveling. For instance, the ingestible device may be designed to increase the frame rate as the speed increases. Images generated by the camera are forwarded to the antenna for transmission to an electronic device located outside of the living body. More specifically, a processor may transmit the images to a transceiver responsible for modulating the images onto the antenna for transmission to the electronic device. In some embodiments, the images are transmitted to the electronic device in real time so that a medical professional can take appropriate action(s) based on the content of the images. For example, the medical professional may discover an area of interest that requires further examination upon reviewing the images. In such a scenario, the propulsion component(s) can orient the propulsive ingestible device so that the camera is focused on the area of interest. Such action may enable the ingestible device to gather additional data (e.g., in the form of images, biological measurements, etc.) regarding the area of interest.

The medical professional may be a general practitioner, specialist (e.g., a surgeon or a gastroenterologist), nurse, or technologist who is responsible for managing the ingestible device as it travels through the living body. Unlike conventional endoscopies, however, the medical professional need not be located in close proximity to the patient (also referred to as a "subject") undergoing examination. For example, the medical professional may examine images generated by the camera on an electronic device located in a remote hospital while the patient lies in another environment, such as a home, battlefield, etc. In this way, capabilities of a traditional GI department may be extended using the technologies described herein.

Embodiments may be described with reference to particular capsule shapes, propulsion components, sensors, networks, etc. However, those skilled in the art will recognize that the features of these embodiments are equally applicable to other capsule shapes, propulsion components, sensors, networks, etc. For example, although a feature may be described in the context of an ingestible sensor that has multiple propellers arranged in a cross-type configuration, the feature may be embodied in an ingestible sensor having another type of propulsor, or propellers in a different arrangement, or a combination of these variations.

Ingestible Device Overview

FIG. 1 includes a cross-sectional view of an example of an ingestible device 100 designed to monitor in vivo environments as it travels through a living body, such as a human body or an animal body. Note that FIG. 1 and other illustrations in this document are not drawn to scale and are shown significantly enlarged for greater clarity. Because the ingestible device 100 can be designed to propel itself through a living body, the ingestible device 100 may be referred to as a "propulsive device." The ingestible device 100 includes a capsule 102 with a cylindrical body 104 and hydrodynamic, atraumatically shaped ends 106*a-b*. One example of a hydrodynamic, atraumatically shaped end is a rounded shape that does not cause damage upon contacting living tissue, such as the roughly hemispherical ends shown in FIG. 1. This geometric shape may be referred to as a "spherocylinder." While the ingestible device 100 shown in FIG. 1 has roughly hemispherical ends, other hydrodynamically-shaped ends may be included in other embodiments. For example, at least one end of the capsule 102 may be a dome with a flat portion through which light can be guided toward an optical sensor. As another example, at least one end of the capsule 102 may be a truncated cone. At least one end of the capsule 102 may also feature fillets that leave flat or minimally curved surfaces along those end(s). The cylindrical body 104 and hemispherical ends 106*a-b* may collectively be referred to as the "structural components" of the capsule 102. To avoid contamination of an internal cavity defined by the cylindrical body 104 and/or hemispherical ends 106*a-b*, the structural components may be hermetically sealed to one another.

In some embodiments, these structural components comprise the same material. For example, the structural components may comprise plastic (e.g., polyethylene (PE), polyvinyl chloride (PVC), polyetheretherketone (PEEK), acrylonitrile butadiene styrene (ABS), polycarbonate, nylon, etc.), stainless steel, titanium-based alloy, or another biocompatible material. The term "biocompatible," as used herein, means not harmful to living tissue. Biocompatible polymers may be three-dimensional (3D) printed, machined, sintered, injection molded, or otherwise formed around components of the ingestible device 100. In other embodiments, these structural components comprise different materials. For example, the hemispherical end 106*a* in which an optical sensor 110 is mounted may be comprised of a transparent plastic, while the other hemispherical end 106*b* and cylindrical body 104 may be comprised of a polymer or metallic alloy. Moreover, these structural components may include a coating that inhibits exposure of the structural components themselves to the in vivo environment. For example, these structural components may be coated with silicone rubber, diamond-like carbon, Teflon, or some other biocompatible, hydrophobic, or hydrophilic coating that aids in safety, durability, or operational efficiency of the ingestible device 100. Additionally or alternatively, these structural components may be coated with an antibacterial material, such as antibiotic-loaded polymethyl methacrylate (PMMA).

As shown in FIG. 1, at least one hemispherical end 106*a* can include an opening 108 through which the field of view of an optical sensor 110 extends. In some embodiments, the opening 108 is filled with a transparent material, such as glass or plastic. Alternatively, the optical sensor 110 may be positioned such that its outermost lens substantially aligns with the exterior surface of the hemispherical end 106*a*, or the optical sensor 110 may be positioned such that the focal length of the lens is similar to the radius of the hemispherical end 106*a* such that focus is ensured for any anatomy that directly contacts the ingestible device 100. While the hemispherical end 106*a* shown in FIG. 1 includes a single opening, other embodiments of the hemispherical end 106*a* may include multiple openings (e.g., for multiple optical sensors, biometric sensors, or combinations thereof). In some embodiments, the hemispherical end 106*a* is entirely comprised of a transparent material. In such embodiments, the hemispherical end 106*a* may not include a dedicated opening for the optical sensor 110 since the optical sensor 110 can generate image data using electromagnetic radiation that has penetrated the transparent material. The hemispherical end 106*a* may include surface features that diffuse or direct illumination leaving the ingestible device 100. Moreover, a portion of the hemispherical end 106*a* may be rendered substantially opaque to inhibit or eliminate interval reflections of light that may interfere with the optical sensor 110.

Due to the convenience in manufacturing, the opening 108 will often be circular. However, the opening 108 could have other forms. For example, in some embodiments the opening 108 is rectangular, while in other embodiments the opening 108 has a rectangular portion with circular endpoints. These circular endpoints may be oriented on opposing sides of the hemispherical end 106*a* so that optical sensors positioned beneath the circular endpoints can observe the in vivo environment along both sides of the propulsive ingestible device 100.

In various embodiments, the capsule 102 may have any of a variety of different sizes, such as any of those listed in Table I.

TABLE I

Example sizes of capsules.

| | Size | | | | | | |
|---|---|---|---|---|---|---|---|
| | 000 | 00 | 0 | 1 | 2 | 3 | 4 |
| Internal Cavity Capacity (ml) | 1.37 | 0.91 | 0.68 | 0.50 | 0.37 | 0.30 | 0.21 |
| Length (mm) | 35 | 30 | 29 | 26.5 | 24 | 21.5 | 19.5 |
| Diameter (mm) | 15 | 13.5 | 11 | 7 | 6.5 | 6 | 5.5 |

As shown in FIG. 1, the ingestible device 100 can include four sections having different responsibilities: a payload section 200, a power section 300, a drive section 400, and a propulsion section 500. Each of these sections is described in greater detail below with respect to FIGS. 2, 3, 4, and 5, respectively. While these sections are illustrated as being distinct from one another, the component(s) associated with each section may not necessarily be located within the corresponding box shown in FIG. 1. For example, the power section 300 may include a power distribution unit that extends into the payload section 200, drive section 400, and/or propulsion section 500 to deliver power to component(s) in those sections.

Figure 2B:
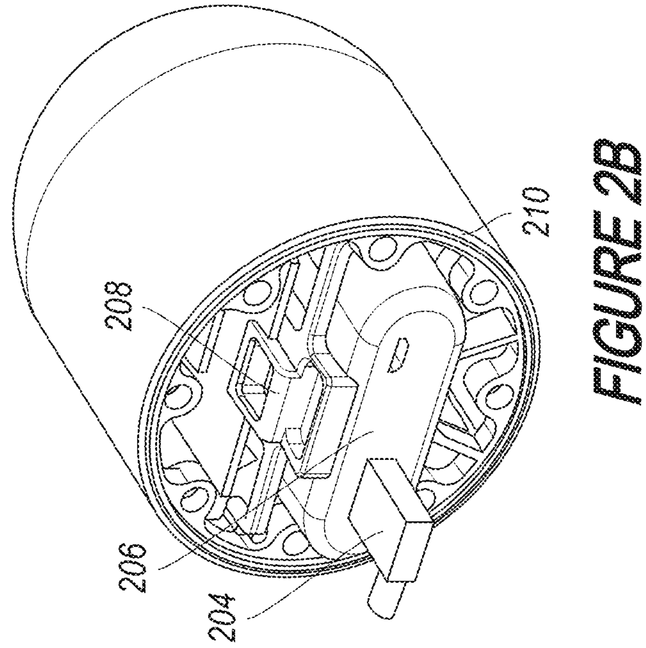
FIG. 2B includes a rear perspective view of the payload section of the ingestible device of FIG. 2A.
Figure 2A:
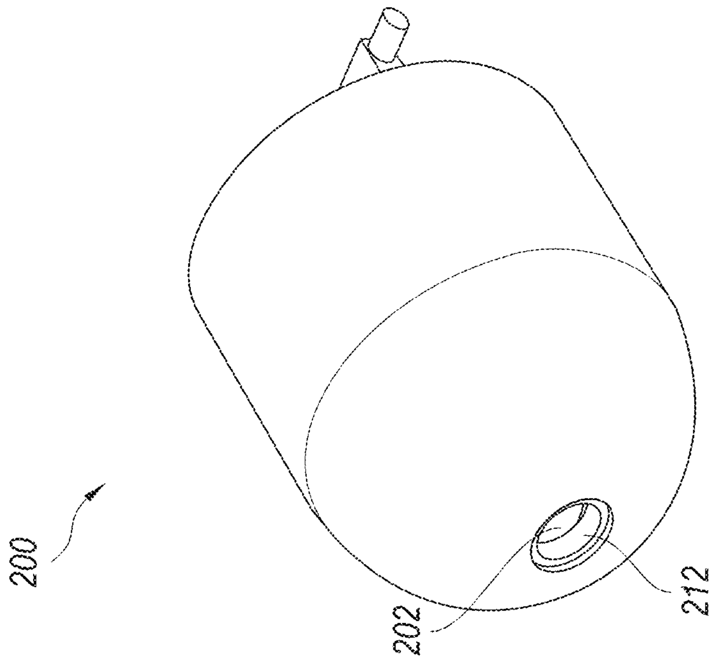
FIG. 2A includes a front perspective view of a payload section of an ingestible device.

FIG. 2A includes a front perspective view of the payload section 200 of the ingestible device, while FIG. 2B includes a rear perspective view of the payload section 200 of the ingestible device. The payload section 200 can include an optical sensor 202, a power and data bus 204, a control unit 206, a manipulator controller 208, a hermetic seal 210, and an illumination source 212. Embodiments of the ingestible device can include some or all of these components, as well as other components not shown here. For example, if the ingestible device has been designed solely for imaging, then the payload section 200 may not include a manipulator controller 208 since no manipulation will be performed.

As the ingestible device traverses the gastrointestinal tract, the optical sensor 202 can generate image data based on electromagnetic radiation reflected by structures located in the gastrointestinal tract. For example, if the optical sensor 202 is a camera, then images or video may be captured as the ingestible device travels through the body. Another example of an optical sensor 202 is an infrared sensor. Other embodiments of the ingestible device may include an acoustic sensor, such as an ultrasonic sonic, instead of, or in addition to the optical sensor 202. Thus, the ingestible device may include one or more sensors configured to generate image data based on energy reflected by structured in the body. An illumination source 212 (also referred to as a "light source") housed in the ingestible device will typically be responsible for generating the electromagnetic radiation. An example of an illumination source 212 is a light-emitting diode (LED). Here, the illumination source 212 is arranged so that the electromagnetic radiation is emitted through the same aperture in the capsule through which the reflected electromagnetic radiation is received. In other embodiments, the illumination source 212 is arranged so that the electromagnetic radiation is emitted through a first aperture in the capsule while the reflected electromagnetic radiation is received through a second aperture in the capsule.

Some embodiments of the propulsive ingestible device include multiple optical sensors 202. For example, an ingestible device may include a camera equipped with a charge-coupled device (CCD) or a complementary metal-oxide-semiconductor (CMOS) sensor assembly capable of detecting electromagnetic radiation in the visible range and an infrared sensor capable of detecting electromagnetic radiation in the infrared range. These optical sensors can generate distinct sets of data that collectively provide meaningful information that may be useful in rendering diagnoses, as well as assisting with spatial positioning. Here, for instance, the infrared sensor may be able to measure the heat emitted by objects that are included in the colored images captured by the camera.

The power and data bus 204 (also referred to as a "bus" or "bus connector") may be responsible for distributing data and/or power to various components in the propulsive ingestible device. For example, the bus 204 may forward image data generated by the optical sensor 202 to the control unit 206, and the control unit 206 may forward the image data to a transceiver configured to modulate the data onto an antenna for transmission to a receiver located outside of the body. As further described below, the receiver may be part of an electronic device on which an individual can view images corresponding to the image data, control the ingestible device, etc. The bus 204 may include cables, connectors, wireless chipsets, processors, etc. In some embodiments, the bus 204 manages data and power on separate channels. For example, the bus 204 may manage data using a first set of cables and power using a second set of cables. In other embodiments, the bus 204 manages data and power on a single channel (e.g., with components capable of simultaneously transferring data and power).

The control unit 206 may be responsible for managing other components in the propulsive ingestible device. For example, the control unit 206 may be responsible for parsing inputs received by the antenna and then providing appropriate instructions to other components in the propulsive ingestible device. As further described below, an individual may provide the input using a controller device (or simply "controller") located outside of the body. The input may be representative of a request to begin generating image data using the optical sensor 202, begin transmitting image data using the antenna, cease generating image data using the optical sensor 202, cease transmitting image data using the antenna, or move the propulsive ingestible device to a desired location. The control unit 206 may include a central processing unit (CPU), graphics processing unit (GPU), application-specific integrated circuit (ASIC), field-programmable gate array (FPGA), microcontroller, logic assembly, or any combination of other similar processing units.

In some embodiments, the propulsive ingestible device is designed to manipulate in vivo environments in some manner. In such embodiments, the payload section 200 could include an intervention component such as a biopsy appendage, needle, cutting mechanism, pushing mechanism, cauterization mechanism (e.g., an ohmic cauterizer or radiofrequency cauterizer), drug delivery mechanism, etc. The manipulator controller 208 can control these intervention components. For example, the manipulator controller 208 may control a biopsy appendage that extends through the capsule to collect tissue based on instructions received from the control unit 206.

To prevent fluids from entering the capsule, the payload section 200 and power section 300 may be hermetically sealed to one another. Accordingly, a hermetic seal 210 may be secured along the interface between the payload section 200 and power section 300. The hermetic seal 210 may be comprised of epoxy resin, metal, glass, plastic(s), rubber(s), ceramic(s), glue or another sealing material. One factor in determining whether the material(s) used to form the hermetic seal 210 are appropriate is whether the surface energy of those material(s) is similar to the surface energy of the substrate to which the hermetic seal 210 is bound. Accordingly, the composition of the hermetic seal 210 may depend on the composition of the structural components of the capsule. For example, if the structural components of the capsule comprise stainless steel, then the hermetic seal 210 may be comprised of an epoxy resin having metal (e.g., stainless steel) particles suspended therein. Alternatively, the hermetic seal 210 may be formed using a flexible gasket, adhesive film, weld, seal, etc.

Figure 3:
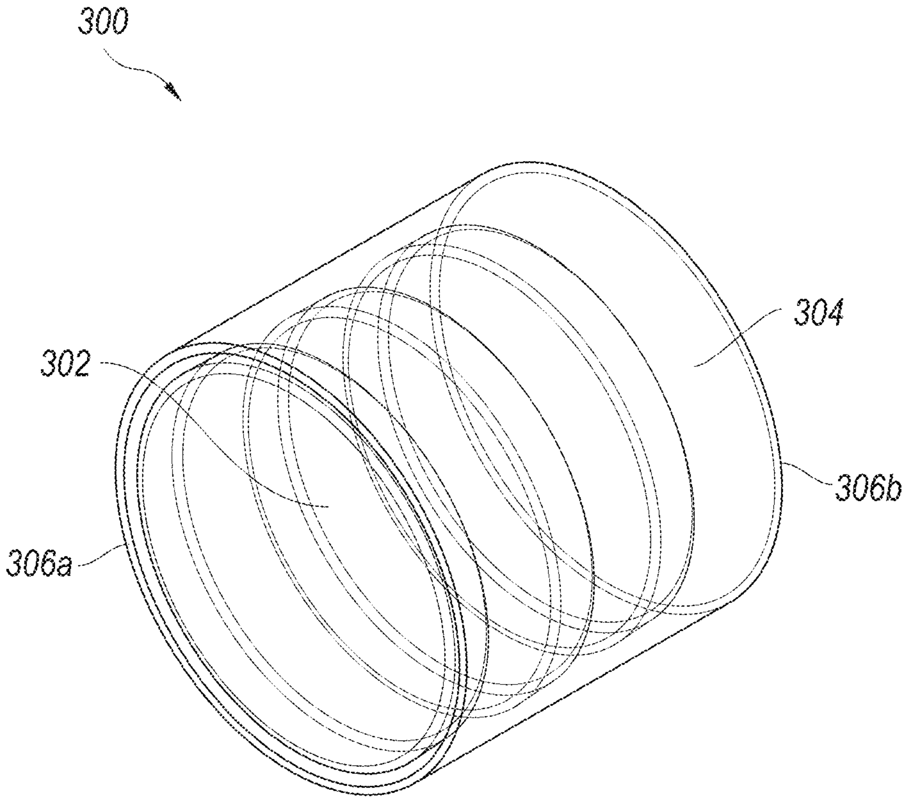
FIG. 3 includes a perspective view of a power section of an ingestible device.

FIG. 3 includes a perspective view of the power section 300 of the ingestible device. The power section 300 can include a power component 302, a power distribution unit 304, and a hermetic seal 306*a-b* secured along each end. The hermetic seals 306*a-b* may be substantially similar to the hermetic seal 210 secured to the payload section 200 as described with respect to FIG. 2. Moreover, the hermetic seal 210 secured to the lower end of the payload section 200 may be the same seal as the hermetic seal 306*a* secured to the upper end of the power section 300. Thus, a single hermetic seal may join the payload section 200 and power section 300.

The power component 302 (also referred to as an "energy storage component") can be configured to supply power to other components of the propulsive ingestible device, such as any optical sensor(s), biometric sensor(s), processor(s), communication components (e.g., transmitters, receivers, transceivers, and antennas), and any other components requiring power. For example, the power component 302 may be responsible for providing power needed by an optical sensor (e.g., optical sensor 202 of FIG. 2) to generate image data. As another example, the power component 302 may be responsible for generating the driving energy to be applied to an antenna to cause wireless transmission of the image data to a receiver located outside of the body.

The power component 302 could be, for example, a silver-oxide battery, nickel-cadmium battery, lithium battery (e.g., with liquid cathode cells, solid cathode cells, or solid electrolyte cells), capacitor, fuel cell, piezoelectric component, or another energy-capture and/or -storage device. In some embodiments, the power component 302 includes one or more battery plates that are exposed to the fluid(s) through which the ingestible device travels. In such embodiments, the power component 302 can be designed to run on a fluid (e.g., a bodily fluid such as stomach acid) that is readily accessible within the in vivo environment for which the ingestible device is designed. Normally, a battery operates by shuttling ions with a positive charge from one place to another through a solution called an electrolyte that has positively- and negatively-charged particles. In the case of exposed battery plates, however, a pair of metal electrodes can be secured to the exterior surface of the ingestible device. One metal electrode (e.g., comprised of zinc) can emit ions into the fluid, which acts as the electrolyte by carrying a small electric current to the other metal electrode (e.g., comprised of copper).

In some embodiments, the power component 302 is designed such that it can wirelessly receive power from a source located outside of the body. In such embodiments, the source can generate a time-varying electromagnetic field that transmits power to the power component 302. The power component 302 can extract power from the electromagnetic field and then supply the power to the other components in the ingestible device as necessary. The power may be received using either the same antenna as is used for data transmission or using a different antenna, inductively coupled coil, or capacitively coupled structure. The source could be the controller used for controlling the ingestible device, the electronic device used for reviewing image data, or some other electronic device (e.g., a mobile phone or a wireless charger belonging to the patient). Alternatively, the wireless power source may be included in an article, such as a belt or band, that can be worn such that the wireless power source is located near the ingestible device as it travels through the living body. Such a wearable article may include a battery pack that is integrated within the article itself or attached to the patient. Moreover, such a wearable article may include one or more antennas for data transmission.

The power component 302 may be designed to fit in a particular segment of the ingestible device. Here, for example, the power component 302 has a button cell form that permits the power component 302 to be secured within the cylindrical body of the capsule. However, other embodiments of the power component 302 may be designed to fit within a hemispherical end of the capsule or another area within the capsule.

As noted above, the power distribution unit 304 may be responsible for distributing power stored in the power component 302 to other components in the ingestible device. Accordingly, component(s) of the power distribution unit 304 may extend into the payload section 200, drive section 400, and/or propulsion section 500. For example, the power distribution unit 304 may include cables that are connected to the optical sensor, bus connector, control unit, control sensors, and/or manipulator controller that may be located in the payload section 200. The power distribution unit 304 may also include component(s) for regulating, stabilizing, or modifying the power to be distributed. Examples of such components include voltage regulators, converters (e.g., DC-to-DC converters), metal-oxide-semiconductor field-effect transistors (MOSFETs), capacitors, transformers, resistors, or inductors.

Figure 4:
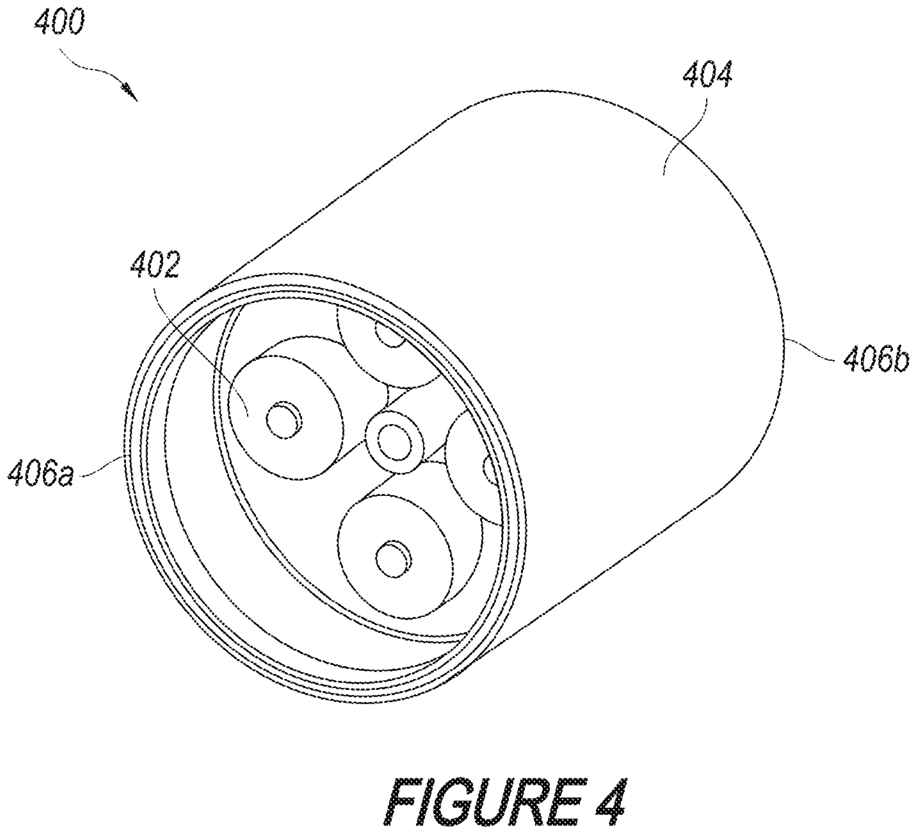
FIG. 4 includes a perspective view of a drive section of an ingestible device.

FIG. 4 includes a perspective view of the drive section 400 of the ingestible device. The drive section 400 can include energy-to-movement converter(s) 402, heat transfer component(s) 404, and a hermetic seal 406*a-b* secured along each end. The hermetic seals 406*a-b* may be the same as or substantially similar to the hermetic seal 210 secured to the payload section 200 as described with respect to FIG. 2. Moreover, the hermetic seal 306*b* secured to the lower end of the power section 300 may be the same seal as the hermetic seal 406*a* secured to the upper end of the drive section 400. Thus, a single hermetic seal may join the power section 300 and drive section 400.

Upon receiving power from a power distribution unit (e.g., the power distribution unit 304 of FIG. 3), the mechanical power converter(s) 402 can drive another component of the ingestible device. Here, for instance, the drive section 400 includes multiple motors, and each motor may be responsible for driving a different propulsor. Examples of motor(s) 402 include DC or AC electric motors, drivers comprised of a shape-memory alloy, electromagnets, shafts, piezoelectric components, etc. The propulsor may be connected to the motor by one or more shafts, gears, levers, bearings, etc.

Components in the ingestible device may produce heat that should be dissipated to avoid causing damage within the body. For example, components such as energy-to-movement converters and motor housings may generate heat if the propulsor(s) are driven for an extended period of time. Accordingly, these components may include or be connected to heat transfer component(s) 404 that are able to assist in dissipating this heat. In some embodiments, the heat transfer component(s) 404 discharge the heat directly into the fluid (e.g., water, bile, stomach acid, and mixtures thereof) surrounding the ingestible device. For example, the motor housings may be comprised of a material (e.g., stainless steel) having acceptable thermal conductivity to promote dissipation of heat. In other embodiments, the heat transfer component(s) 404 discharge the heat into the capsule. When heat is discharged into the capsule, the heat may naturally transfer into the fluid surrounding the ingestible device through conduction and convection.

Figure 5B:
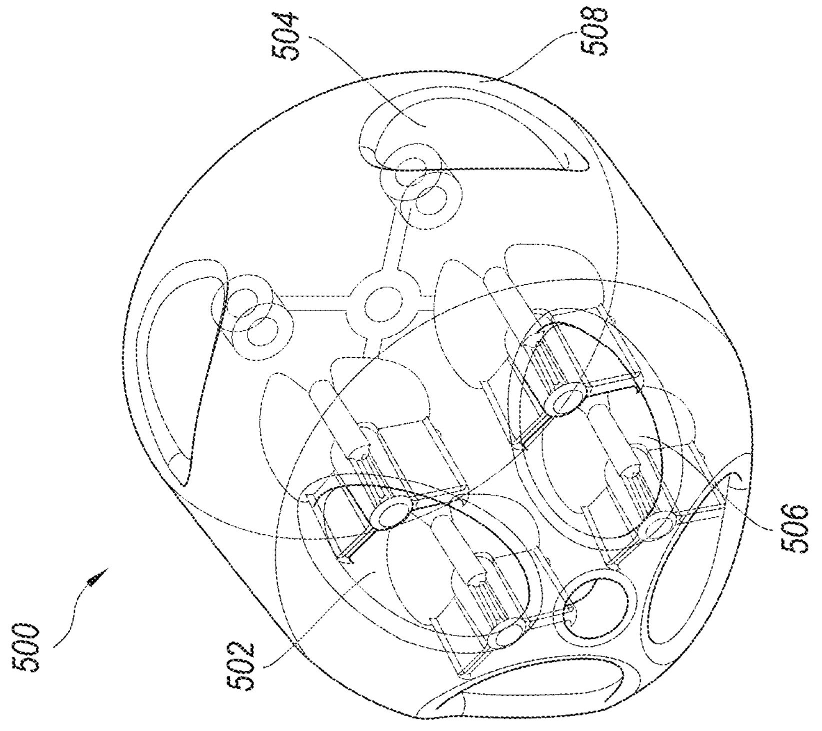
FIG. 5B includes a transparent perspective view of the propulsion section of the ingestible device of FIG. 5A.
Figure 5A:
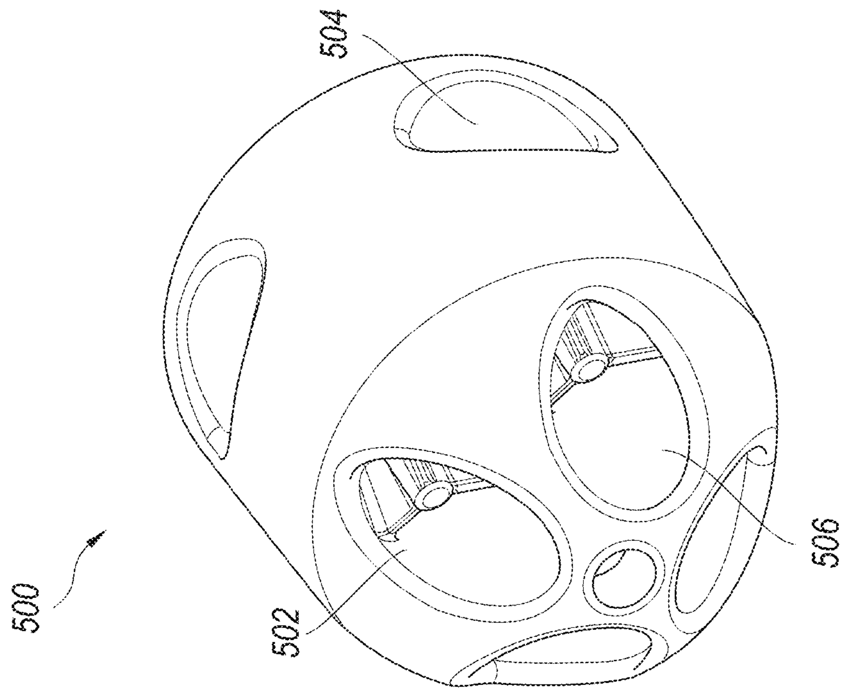
FIG. 5A includes a perspective view of a propulsion section of an ingestible device.

FIG. 5A includes a perspective view of the propulsion section 500 of the ingestible device, while FIG. 5B includes a transparent perspective view of the propulsion section 500 of the ingestible device. The propulsion section 500 can include one or more propulsors 502, one or more intakes 504, and a hermetic seal 508 secured along its upper end. The hermetic seal 508 may be substantially similar to the hermetic seal 210 secured to the payload section 200 as described with respect to FIG. 2. Moreover, the hermetic seal 508 may be the same seal as the hermetic seal 406*b* secured to the lower end of the drive section 400. Thus, a single hermetic seal may join the drive section 400 and propulsion section 500.

As noted above, the ingestible device may include one or more propulsion components (also referred to as "propulsion systems" or "thrust components"). Each propulsion component can include a propulsor configured to generate a propulsive force for moving the ingestible device and an energy-to-movement converter configured to supply motive power to the propulsor. Here, for example, the propulsion section 500 includes four rotors 502 that are driven by four motors located in the drive section 400. In some embodiments, each propulsor is driven by a different mechanical power converter. In other embodiments, multiple propulsors may be driven by a single energy-to-movement converter. For example, a single motor may be responsible for supplying motive power to multiple propulsors, though the speed of each propulsor may be varied through a mechanical connection (e.g., a clutch system or a gear system).

As further described below, multiple propulsors 502 can be arranged to facilitate movement along different axes. In FIGS. 5A-B, for example, four propulsors 502 are arranged radially about a central axis 516 defined through the capsule in a cross-type configuration. More specifically, these propulsors 502 are disposed at locations radially offset from the central axis and at different angular offsets about the central axis. By independently driving these propulsors 502, movement can be achieved in any direction or orientation, in a fashion similar to a quadcopter. Accordingly, the ingestible device may be commanded to move forward and backward at different speeds. Moreover, the ingestible device may be commanded to change its orientation through rotation about three mutually perpendicular axes. These changes in orientation and forward/backward motions can be converted into variations in yaw (normal axis), pitch (transverse axis), and roll (longitudinal axis), and therefore movement to any location can be represented in three-dimensional space.

In FIGS. 5A-B, the propulsors 502 are rotors capable of drawing fluid through intakes 504 formed in the capsule. The term "rotor," as used herein, refers to a component that is capable of rotating to create propulsive force. An example of a rotor is a propeller. However, other propulsors could be used instead of, or in addition to, the rotors. Examples of propulsion components include helicoids, fins, lash-like appendages (also referred to as "flagellum"), undulating mechanisms, etc. Moreover, propulsion components could be arranged along the cylindrical body of the capsule instead of, or in addition to, in the hemispherical end of the capsule. For example, an ingestible device may include oscillating fins arranged along opposing sides of the cylindrical body of the capsule. These oscillating fins may be used in conjunction with propeller(s), helicoid(s), or lash-like appendage(s) located in the hemispherical end of the capsule to provide greater control over the movement of the ingestible device.

As shown in FIGS. 5A-B, the capsule may include one or more channels through which fluid can be drawn by the propulsion(s) 502. Each channel includes an inlet 504 through which fluid can be drawn and an outlet 506 through which the fluid is discharged. Examples of inlets 504 include ducts, lumens, vanes, tubes, etc. While the embodiment shown in FIG. 5 includes an identical number of propulsors 502 and inlets 504, that need not always be the case. For example, a propeller mounted in the hemispherical end of the capsule may be able to draw fluid through one or more inlets to prevent moving components, such as the propulsor(s) 502, from touching living tissue. Rotational propeller efficiency may be optimized with fixed stator vanes so as to control swirl, increase velocity, and increase controllability, as further discussed below with respect to FIGS. 5C-D. In some embodiments, coaxial contra-rotating propellers may be used to obviate fixed stator vanes altogether. Propeller and vane blade count and geometry may be tuned to optimize clearing of bubbles and debris as a function of diameter, speed, and fluid properties.

In some embodiments, a filter is placed in at least one of the channels defined through the capsule. For example, a filter may be secured in each channel defined through the capsule. Filters may be necessary to ensure that objects suspended in the fluid drawn through the inlets 504 that exceed a particular size are removed. For example, if the ingestible device is designed for use within the gastrointestinal tract, the filter(s) may be designed to prevent solid particulates such as food particles from contacting the propulsor(s) 502.

Figure 5C:
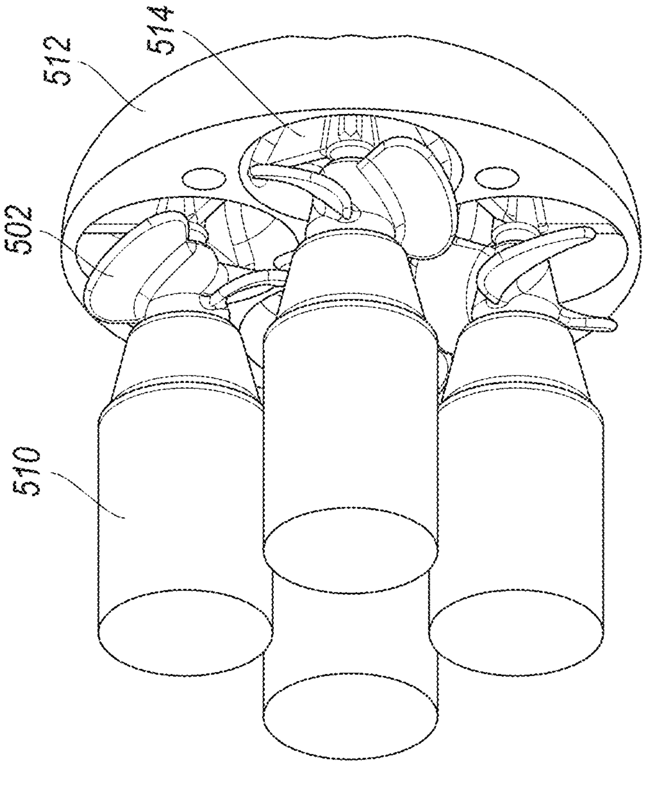
FIG. 5C illustrates how propulsors may be arranged adjacent to stator blades in a distal element of an ingestible device.

Another issue is that propulsors tend to impart rotational motion on (or "stir") the fluid rather than create thrust unless designed properly. This problem can be addressed by adding one or more stator vanes (also referred to as "stator blades") to each flow channel. The terms "stator vane" and "stator blade" refer to a fixed blade positioned within the flow channel through which fluid is drawn and then ejected by a propeller. FIG. 5C illustrates how propulsor(s) 502 may be arranged adjacent to stator vanes 514 in a distal element 512 of the ingestible device of FIGS. 5A-B. These stator vanes 514 may serve to straighten the fluid flow, reduce the stirring effect, and increase thrust and thrust consistency. As shown in FIG. 5C, each propulsor 402 may be connected to a separate motor housing 510 in which the motor responsible for driving the propulsor is located. The propulsors 502 (and thus the motor housings 510) may be arranged in a cross-type configuration to better control the propulsive force.

Figure 5D:
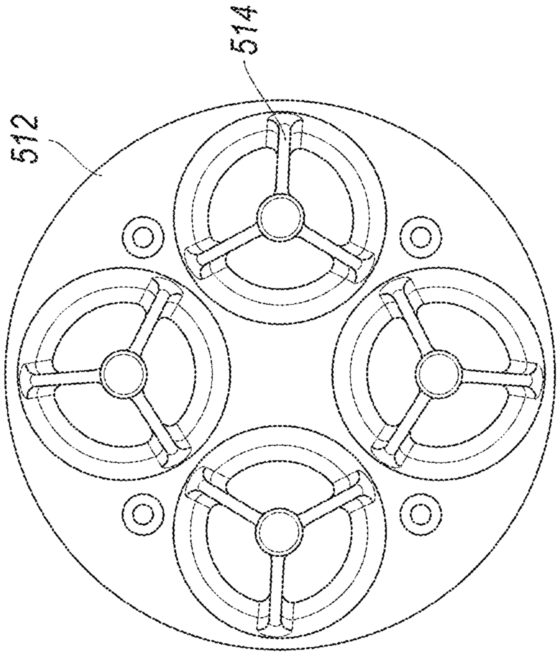
FIG. 5D is an isolated rearward view of the distal element of FIG. 5C.

FIG. 5D is an isolated, rearward view of the distal element 512 shown in FIG. 5C. In embodiments where the distal element 512 includes multiple stator vanes 514, the stator vanes 514 may be radially arranged around a geometric center of the distal element 512. Generally, the stator vanes 514 are arranged roughly evenly about the geometric center as shown in FIG. 5D. However, in some embodiments, the stator vanes 514 are arranged about the geometric center in an uneven manner.

Figure 6A:
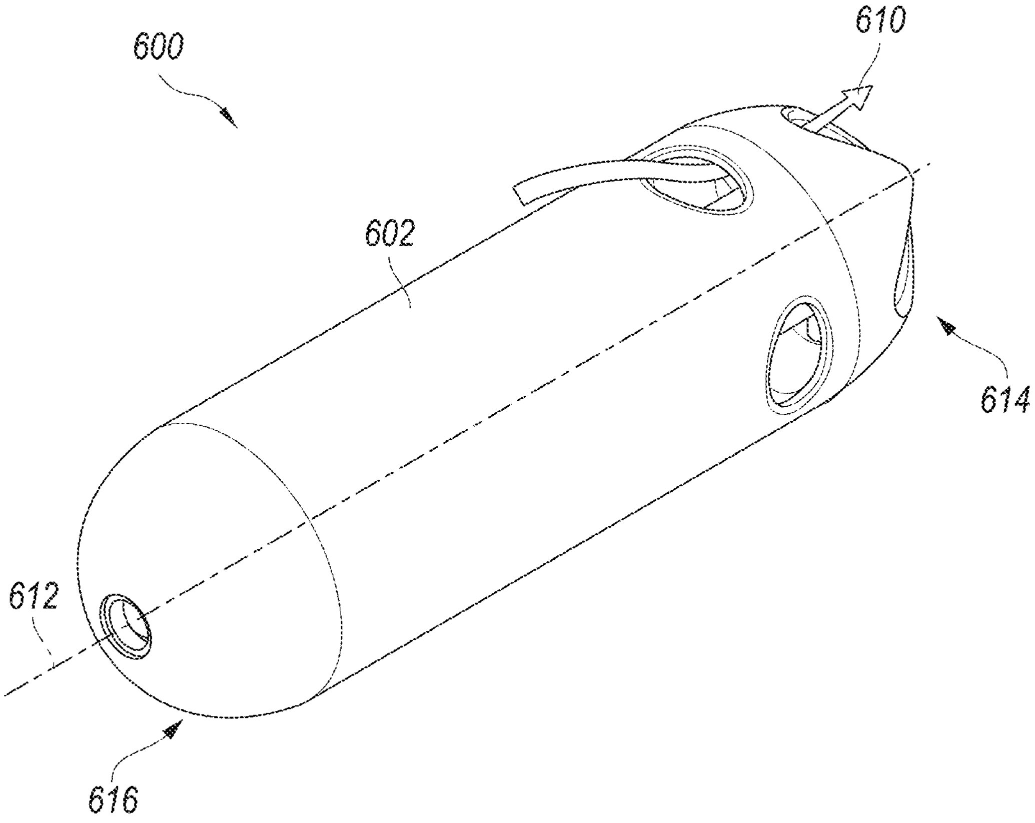
FIG. 6A includes a perspective view of an ingestible device having a rounded structural body with a central axis therethrough.
Figure 6B:
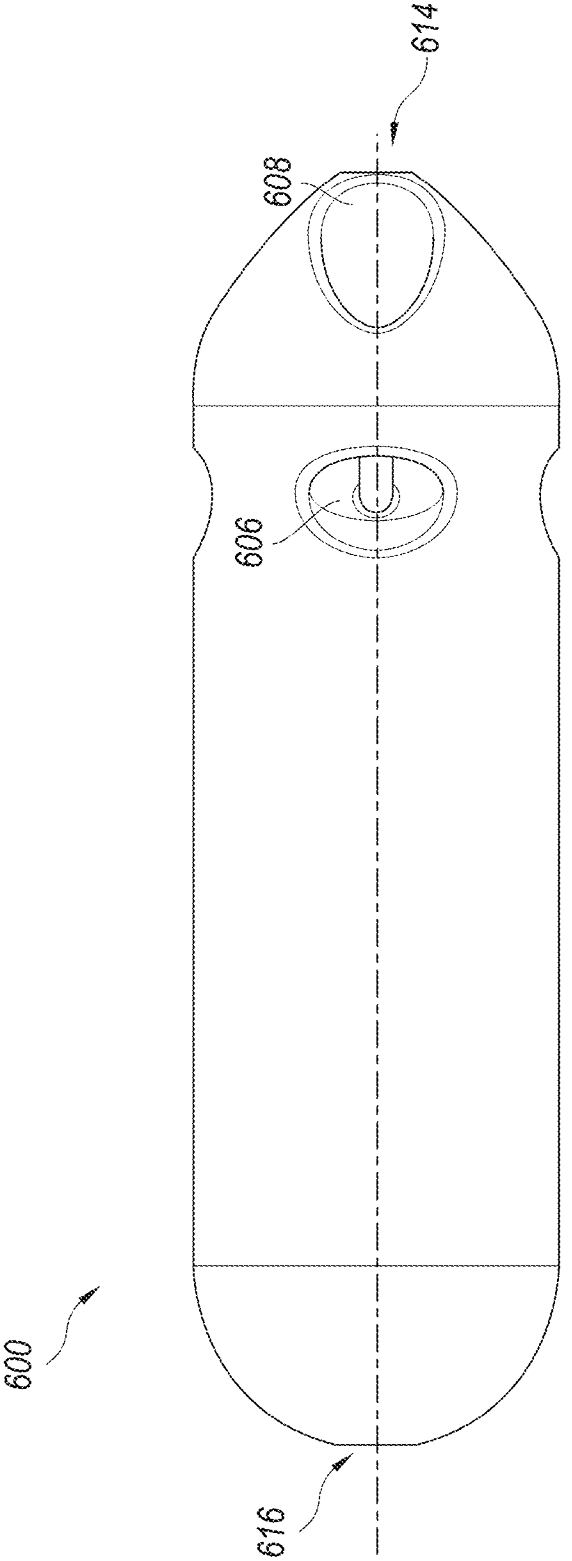
FIG. 6B includes a side view of the ingestible device of FIG. 6A.
Figure 6C:
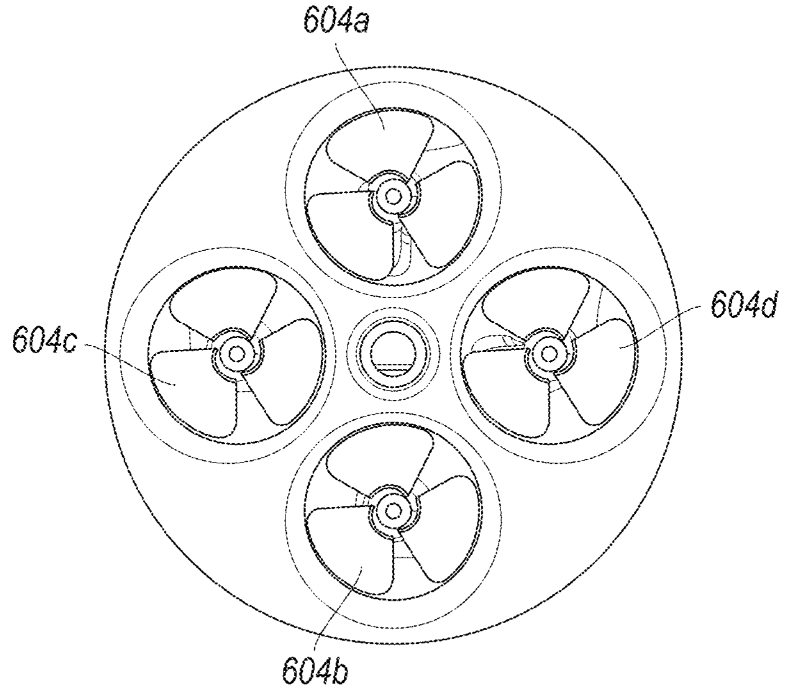
FIG. 6C includes a rear view of the ingestible device of FIG. 6A.

FIGS. 6A-C include perspective, side, and rear views of an ingestible device 600 having an atraumatic structural body 602 with a central axis 612 therethrough. The structural body 602 shown in FIGS. 6A-C is a spherocylinder that includes a cylindrical segment interconnected between hemispherical segments. In other embodiments, the structural body 602 may be in the shape of an oval, rectangle, teardrop, etc.

As noted above, the ingestible device 600 can include one or more propulsors for controlling movement along three mutually perpendicular axes. Here, for example, the ingestible device 600 includes four rotors 604*a-d* arranged radially about the structural body 602 orthogonal to the central axis 612. The four rotors 604*a-d* may include a first pair of rotors 604 *a-b* arranged radially opposite each other relative to the central axis 612 and a second pair of rotors 604 *c-d* arranged radially opposite each other relative to the central axis. Each pair of rotors may be configured to share identical chirality; for example, rotors 604*a-b* may both generate forward thrust when rotating clockwise relative to the central axis 612. Simultaneously, the rotor pairs may be configured to have opposite chirality; for example, rotors 604*a-b* may generate forward thrust while rotors 604*c-d* may generate backward thrust when all four rotors are rotating clockwise relative to the central axis 612. As shown in FIG. 6C, the first and second pairs of rotors 604*a-d* may be arranged in a cross-type configuration so that neighboring rotors rotate in opposite directions to produce thrust in the same direction, while radially opposite rotors rotate in the same direction to produce thrust in the same direction. Such a configuration allows independent control of thrust, pitch, yaw, and roll through the combination of the effects of the individual rotors; thus, control of position and orientation may be achieved in a fashion similar to a quadcopter.

Each rotor may be located in a different channel defined through the structural body 602, and each channel may include an inlet 606 through which fluid is drawn by the corresponding rotor and an outlet 608 through which the fluid is discharged by the corresponding rotor. Generally, the channels are defined through the structural body 602 in a direction substantially parallel to the central axis. Here, for example, the inlet 606 of each channel is located in a cylindrical segment of the structural body 602 while the outlet 608 of each channel is located in a hemispherical segment of the structural body 602. When in operation, the rotors 604*a-d* can draw fluid through the inlets 606 to create flows 610 that propel the ingestible device in a particular direction. In some embodiments, the channels are tapered. For example, the inlet 606 of each channel may have a smaller diameter than the outlet 608, or the inlet 606 of each channel may have a larger diameter than the outlet 608.

In some embodiments, each rotor is designed to rotate in a primary direction and a secondary direction. For example, the first pair of rotors 604*a-b* may be configured to be able to rotate in the clockwise and counterclockwise directions in relation to the central axis 612. Similarly, the second pair of rotors 604*c-d* may be able to rotate in the counterclockwise and clockwise directions in relation to the central axis 612. Accordingly, while the flows 610 are shown as flowing toward a first end 614 (also referred to as the "distal end") of the ingestible device 600, the flows 610 could instead be flowing toward a second end 616 (also referred to as the "proximal end") of the ingestible device 600.

As noted above, the term "rotor," as used herein, refers to a component that is capable of rotating to create propulsive force. The propulsive force imparts momentum to the surrounding fluid(s) to produce movement. The structural body 602 can be fitted with one, two, three, four, or more rotors depending on the speed and maneuvering requirements of the ingestible device 600. In FIGS. 6A-C, for example, four rotors are arranged in a cross-type configuration within the first end 614 of the structural body 602. In other embodiments, three rotors are arranged in a triangular configuration within the first end 614 of the structural body 602.

Each rotor may be independently driven by a different motor. In FIGS. 6A-C, for example, the ingestible device 600 includes four motors configured to supply motive power to the four rotors 604*a-d*. In other embodiments, multiple rotors may be driven by a single mechanical power converter. For example, a single motor may be responsible for supplying motive power to the first pair of rotors 604*a-b*, though the speed of these rotors may be varied through a mechanical connection (e.g., a clutch system or a gear system).

In some embodiments, each rotor has a fixed pitch. In FIGS. 6A-C, for example, the four rotors 604*a-d* are fixedly arranged along a radial plane orthogonal to the central axis 612. In other embodiments, at least one rotor has a variable pitch. In such embodiments, greater control over movement of the ingestible device 600 can be achieved by simultaneously controlling the pitch and rotation of the rotors 604*a-d*.

The rotors may consist of one or more biocompatible materials. Examples of biocompatible materials include titanium alloys, stainless steel, ceramics, polymers, fiber-reinforced polymers (e.g., fiberglass or carbon fiber) plastics (e.g., polycarbonate, nylon, PEEK, or ABS), resins, composites, etc. Moreover, each rotor may have an antibacterial, hydrophobic, or hydrophilic coating applied thereto. For example, each rotor may be coated with antibiotic-loaded PMMA. The coating(s) applied to the rotors may depend on the type of in vivo environment for which the ingestible device 600 is designed.

Generally, to produce a rotor, a number of blades are secured to the hub through welding, gluing, or, alternatively, by forging the entire rotor in one piece. The number of blades may depend on the desired efficiency, speed, acceleration, maneuverability, etc. For example, 3-blade rotors exhibit good acceleration in comparison to other types of rotors, while 4-blade rotors exhibit good maneuverability in comparison to other types of rotors. Rotors with a higher blade count (e.g., those with 5 or 6 rotor blades) exhibit good holding power in turbulent in vivo environments, such as those with high flow rates. A single-blade rotor may have advantages in manufacturability and durability. In the embodiment shown in FIGS. 6A-C, each rotor includes three helicoidal surfaces acting together to rotate through a fluid (e.g., water, bile, etc.) with a screw effect.

One of the difficulties of producing thrust at small scales is the persistent bubbles that can get trapped near rotors such as propellers, preventing the rotors from properly engaging with the fluid. This problem can be addressed by carefully designing the shape, number, and arrangement of blades along each rotor to assist in the clearing of bubbles. Carefully matching the pitch of the blade, shape of lumens, motor speed, clearance between rotor and wall, clearance between rotor and stator vane, and surface material properties affects the generation and clearing of bubbles.

Rotors may be formed based on simple truncated Archimedes screw geometry. Alternatively, as discussed above, rotors may feature a plurality of individual blades featuring curvature optimized to thrust in the forward or rearward direction. Likewise, if stator blades are positioned in the channels through which the rotors draw and then eject fluid, those stator blades may feature flat or curved blades.

Figure 7B:
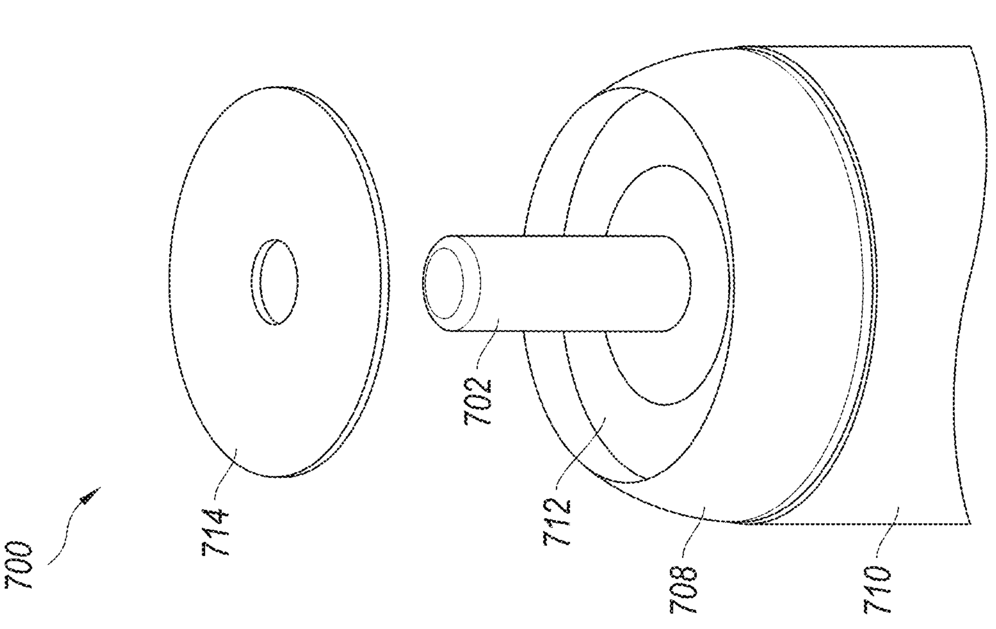
FIG. 7B illustrates how when the seal is potted inside the main seal body, an orifice disc may be secured within the pocket that is formed.
Figure 7A:
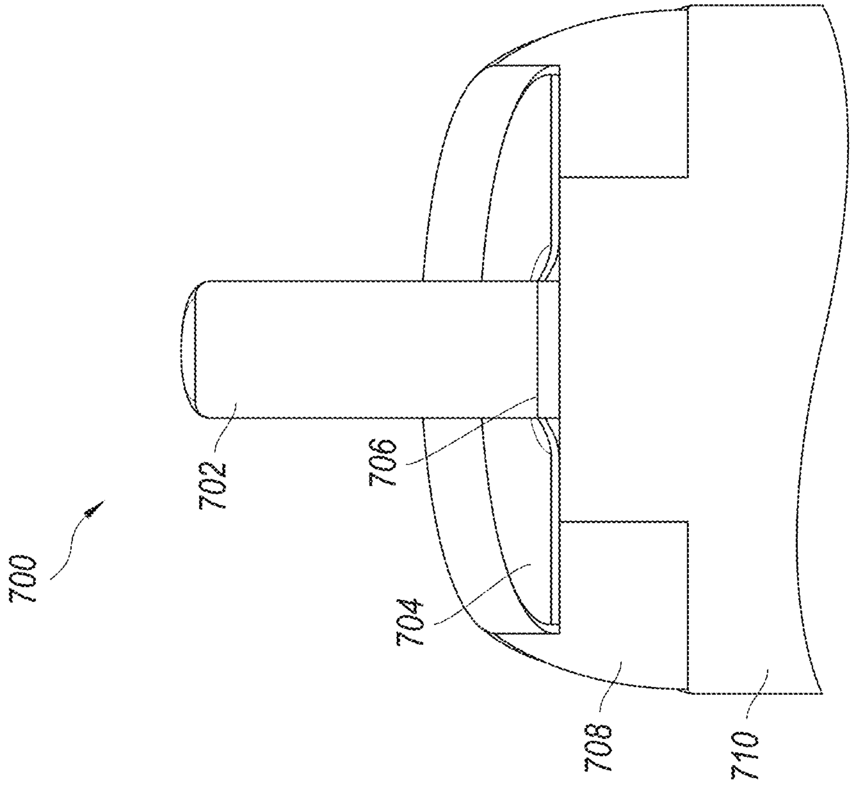
FIG. 7A includes a cross-sectional view of an ingestible device that illustrates how undersizing a seal formed by a punched or drilled sheet compared to the diameter of the motor shaft enables a single contact line to be created between the seal and motor shaft.

Preventing fluid from entering the ingestible device, especially in the propulsion section that includes the moving motor interface, is also critical. Accordingly, the ingestible device may implement tight tolerances, hydrophobic and/or hydrophilic materials, or mechanical seals. Seals can maintain tolerances at the micro scale, and therefore are useful for maintaining safety and consistency without requiring complex assembly processes. FIGS. 7A-B illustrate how low-profile and low-friction seals can be implemented to prevent fluid from entering the motor housing(s) of an ingestible device 700.

FIG. 7A includes a cross-sectional view of the ingestible device 700 that illustrates how undersizing a seal 704 formed by a punched or drilled sheet compared to the diameter of the motor shaft 702 enables a single contact line 706 to be created between the seal 704 and motor shaft 702. Sealing action, static friction, and dynamic friction can be optimized by tuning the dimensional interference and resulting embedded tension. The punched or drilled sheet may be comprised of polytetrafluoroethylene (PTFE) or a similar material (e.g., ultra-high-molecular-weight (UHMW) polyethylene). This design can be readily produced with relatively few machining operations. Another advantage of this approach is that several seals can be produced at once with a simple drilling jig. By under-drilling a small hole (e.g., 0.5-0.6 mm in diameter for a motor shaft that is 0.7 mm in diameter) in the sheet and then dilating it over the motor shaft 702, hoop tension (also referred to as "hoop stress") is produced. The hoop tension will cause the dilated hole to protrude slightly, producing a minimal line of contact 706 with the motor shaft 702 and reducing friction while providing a seal.

The seal 704 can be produced using a hypodermic tubing punch. Multiple seals can be drilled simultaneously on a lathe while still in the hypodermic tube using a simple fixture and drill guide. The assembly process may be completed by placing the seal 704 on the motor shaft 702 and then fixing it in place with a curable adhesive (e.g., a UV-curable adhesive), radio-frequency (RF) welding, heat welding, etc. The seal 704 can be dilated over the motor shaft 702 and then potted inside a main seal body 708 with a curable adhesive or another sealing technology.

As shown in FIGS. 7A-B, the main seal body 708 may be connected to the motor housing 710 with a curable adhesive or another sealing technology. One or more seals may be implemented on a single motor shaft in order to optimize shaft friction and seal reliability. Successive lip seals with different clearances may assist in optimizing energy efficiency, aging, and overall safety and performance. As shown in FIG. 7B, when the seal 704 is potted inside the main seal body 708, a pocket 712 may be formed. An orifice disc 714 having a hole defined therethrough for receiving the motor shaft 702 may be positioned within the pocket to further inhibit leaking into the motor housing 710. The orifice disc 714 may be comprised of plastic, metal, rubber, Viton, Teflon, UHMW polyethylene, high-density polyethylene, or similar materials.

Accordingly, a manufacturer may obtain a flexible substrate having a substantially circular shape, form a hole at a geometric center of the flexible substrate (e.g., by punching or drilling the hole), and then dilate the hole in the flexible substrate around a motor shaft having a larger diameter than the hole. Such an approach may cause an elastic interference fit to be created between the flexible substrate and motor shaft, thereby forming a seal. Then, the manufacturer may secure the flexible substrate along an outer perimeter to form a hermetic seal. For example, as noted above, the flexible substrate could be secured with a curable adhesive, RF welding, heat welding, etc.

Figure 8A:
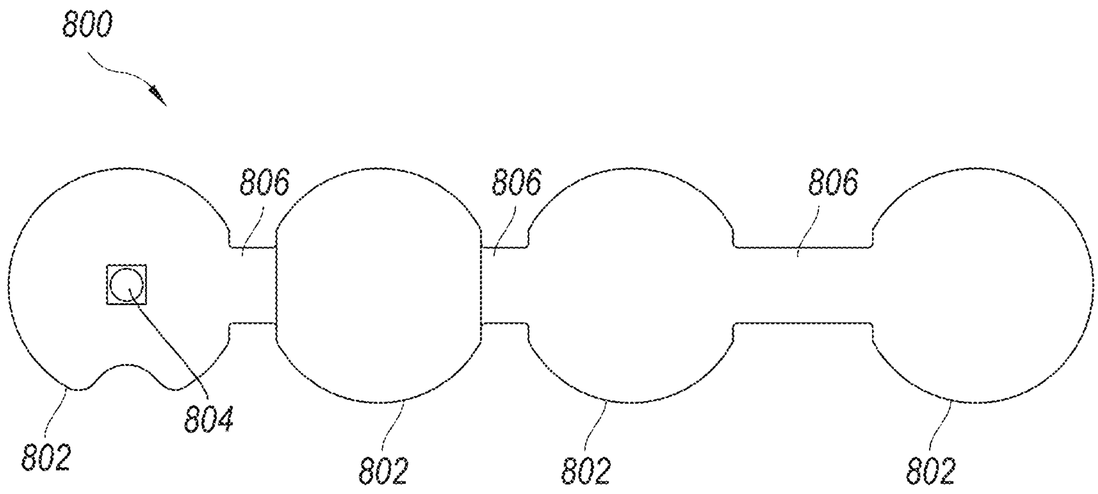
FIG. 8A depicts an example of a flexible printed circuit board assembly (PCBA) in an expanded form.
Figure 8B:
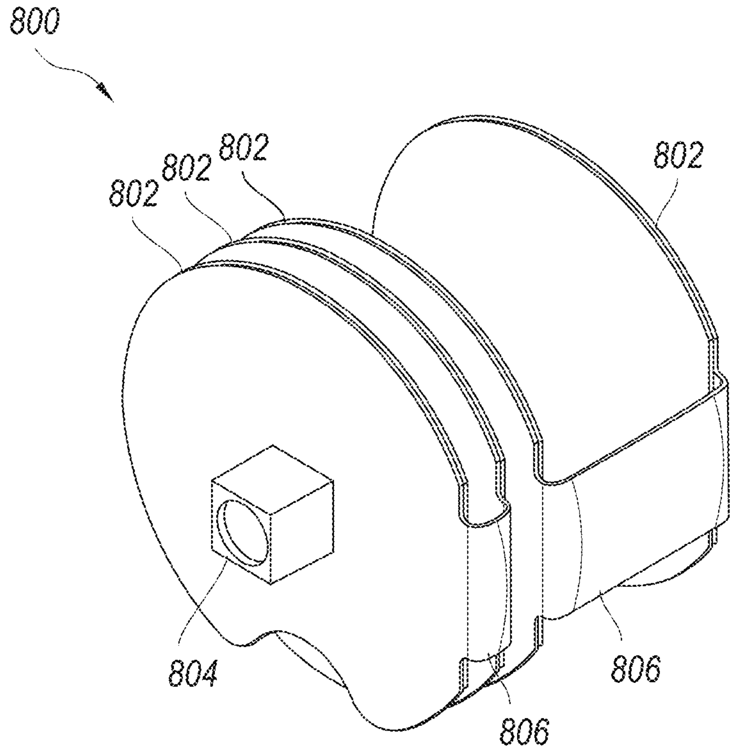
FIG. 8B depicts the flexible PCBA of FIG. 8A in a folded form.

Some or all of the electronic components described herein as being contained within an ingestible device may be mounted on flexible printed circuit board assemblies (PCBAs). FIGS. 8A-B depict an example of a flexible PCBA 800 in its expanded and folded forms, respectively. As shown in FIG. 8A, the flexible PCBA can include at least two rigid areas 802 that serve to provide support to components 804 mounted thereon and accompanying solder joints, as well as to help define the structure of the PCBA 800 as a whole. These rigid areas 802 may be connected by flexible areas 806 that can be folded to allow the PCBA 800 to fit within the ingestible device. The PCBA 800 may include conductive connections between the electronic components to allow for the transfer of power and/or data therebetween. More specifically, the PCBA 800 may include one or more conductive layers that serve as connections between the electronic components mounted to the rigid areas 802. Each pair of conductive layers may be separated by an insulating layer (also referred to as a "non-conductive layer") comprised of a non-conductive material such as polyimide.

Figure 9:
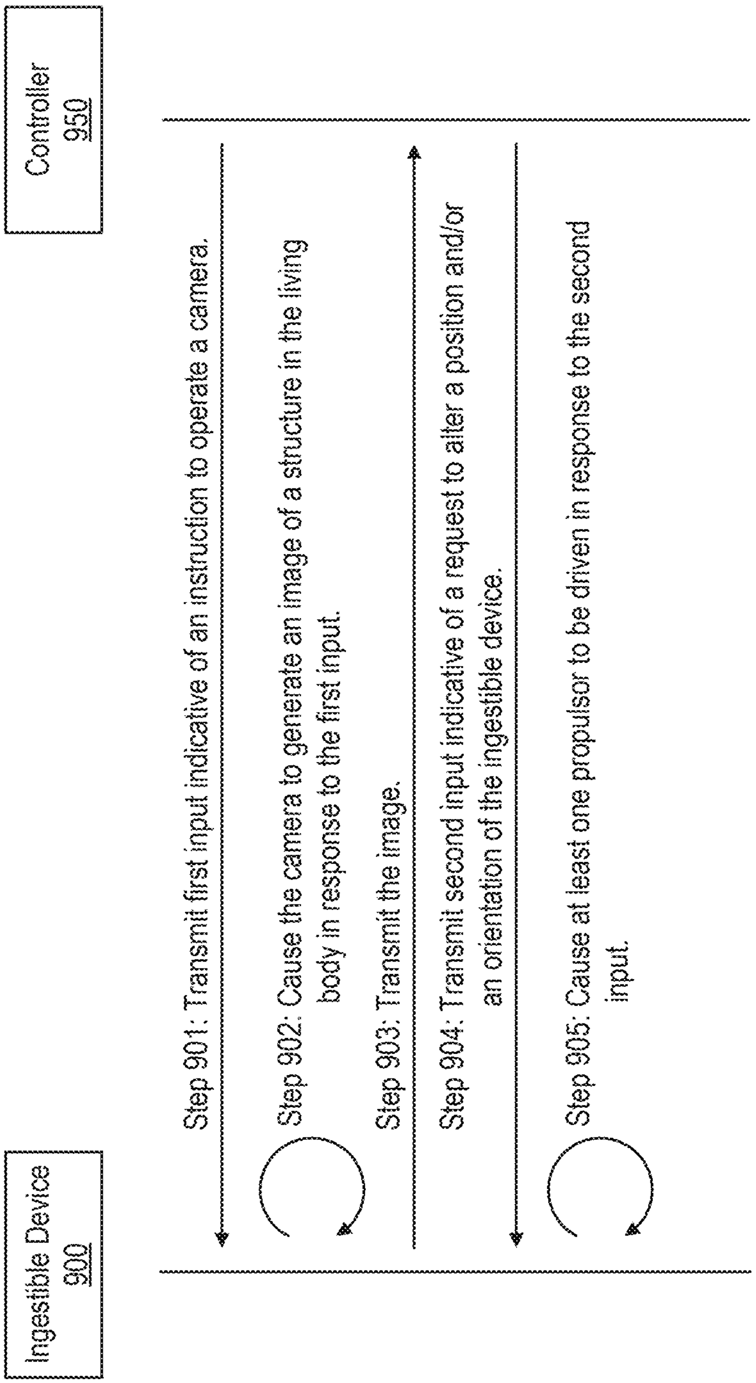
FIG. 9 includes a high-level illustration of communications between a device designed for ingestion by a living body and a controller through which movement of the ingestible device is controlled.

FIG. 9 includes a high-level illustration of communications between a device 900 designed for ingestion by a living body and a controller 950 through which movement of the ingestible device 900 is controlled. Because images generated by the ingestible device 900 may be reviewed on the controller 950, the controller 950 could also be referred to as a "data review station" or "data review unit." Initially, the controller 950 transmits first input indicative of an instruction to operate a camera housed within the ingestible device 900 (step 901). Alternatively, the ingestible device 900 may be designed to automatically operate the camera when the device is first powered on or activated by removal from the packaging.

The ingestible device 900 can cause the camera to generate an image of a structure in the living body in response to the first input (step 902). The structure may be a biological structure or a non-biological structure (also referred to as a "foreign object"). The ingestible device 900 can then transmit the image to the controller 950 for review (step 903). More specifically, a processor responsible for processing images generated by the camera may forward the image to a transmitter for modulation onto an antenna for wireless transmission to the controller. In some embodiments, the transmitter is part of a transceiver capable of transmitting communications to, and receiving communications from, the controller 950.

The controller 950 may further transmit second input indicative of a request to alter a position and/or an orientation of the ingestible device 900 (step 904). This second input may be referred to as a "steering instruction" or a "propulsion instruction." The ingestible device 900 can cause at least one propulsor to be driven in response to the second input (step 905). In instances where multiple propulsors are driven in response to the second input, the ingestible device 900 may generate multiple signals for driving the multiple propulsors. These signals may be different than each other. For example, each propulsor of the multiple propulsors could be rotated at different speeds. As another example, some propulsors of the ingestible device 900 may be rotated while other propulsors of the ingestible device 900 are held stationary.

Figure 10:
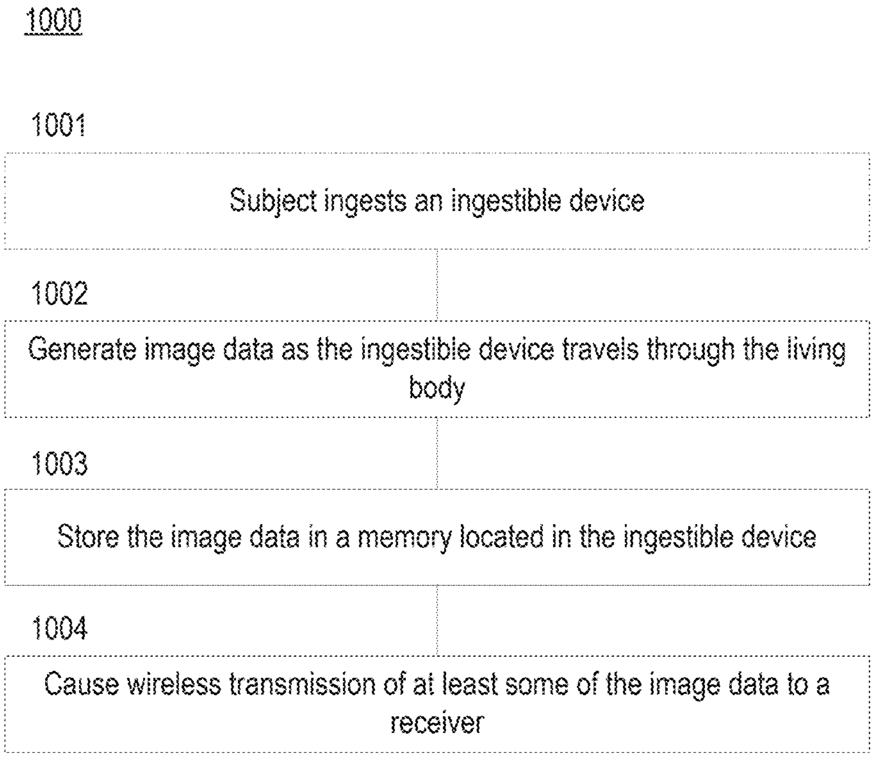
FIG. 10 depicts a flow diagram of a process for monitoring an in vivo environment using a device designed for ingestion by a living body.

FIG. 10 depicts a flow diagram of a process 1000 for monitoring an in vivo environment using a device designed for ingestion by a living body. Initially, a subject ingests the ingestible device as part of a capsule endoscopy procedure for observing the gastrointestinal tract (step 1001). The ingestible device (and its controlling software) may support several different data collection modes. For instance, the ingestible device may support a "general mode" suitable for open navigation and/or a "swallow mode" suitable for one-way trips through the esophagus.

An optical sensor included in the ingestible device can then begin generating image data as the ingestible device travels through the living body (step 1002). In some embodiments, the ingestible device causes the optical sensor to begin generating image data in response to receiving an instruction to do so. The instruction may be submitted, for example, by an operator through a controller that is communicatively coupled to the ingestible device. In other embodiments, the ingestible device causes the optical sensor to automatically generate image data in response to determining that a predetermined criterion has been met. For example, the ingestible device may cause the optical sensor to begin generating image data in response to determining that the ingestible device has entered a particular in vivo environment. The ingestible device may reach such a determination by examining biometric data generated by a biometric sensor. For instance, the ingestible device could establish whether it is presently within the stomach by examining biometric data representative of pH measurements. The images may be captured with any of various resolutions, such as 48×48 pixels, 320×240 pixels, or 640×480 pixels. In other embodiments, images may be captured with higher or lower resolutions. The image data may be stored, at least temporarily, in memory located in the ingestible device (step 1003).

The ingestible device can then cause wireless transmission of at least some of the image data to a receiver located outside of the living body via an antenna (step 1004). In some embodiments, the receiver is housed within an electronic device associated with the subject. For example, the image data may be transmitted to a mobile phone associated with the subject, and the mobile phone may forward the image data to another electronic device for review by the operator responsible for controlling the ingestible device. In some embodiments, image data is transmitted to the receiver on a periodic basis (e.g., every 3 seconds, 5 seconds, 30 seconds, 60 seconds, etc.). In other embodiments, image data is transmitted to the receiver in real time. That is, the ingestible device may stream image data to the receiver as the image data is being generated by the optical sensor.

To reduce the amount of raw data that must be transferred across the bus or wireless link, the image data (and well as identifying data, telemetry data, etc.) may be compressed in such a way as to reduce the quantity without significantly affecting user perception of quality. For example, algorithms may be employed that reduce color/hue differently than intensity, or reduce high-frequency content differently than low-frequency content. Standardized image and/or video compression algorithms such as JPEG, H.264 (MPEG), H.265, and the like may be employed to compress the data. To further reduce the amount of data, the image resolution may be reduced before it is compressed and transmitted. For example, the optical sensor may generate an image with 640×480 pixel resolution, but the image may be downsampled to 320×240 pixel resolution prior to JPEG compression. The resolution may be adjusted during operation to achieve a desired tradeoff between image quality and frame rate (e.g., image quality may be reduced in order to increase frame rate while the ingestible device travels through the esophagus). Other compression algorithms may be used after the data has been transmitted over the wireless link, such as in the case where the data is transmitted to a controller that has computing and memory resources available for executing more demanding compression algorithms than is feasible to perform on the ingestible device itself. This additional compression may be used to reduce the size of data that is stored on the controller or some other electronic device. Data may be encrypted, on the ingestible device, the controller, or some other electronic device, to prevent unauthorized third-party access of patient identifying information (PII) or medically sensitive information.

Figure 11:
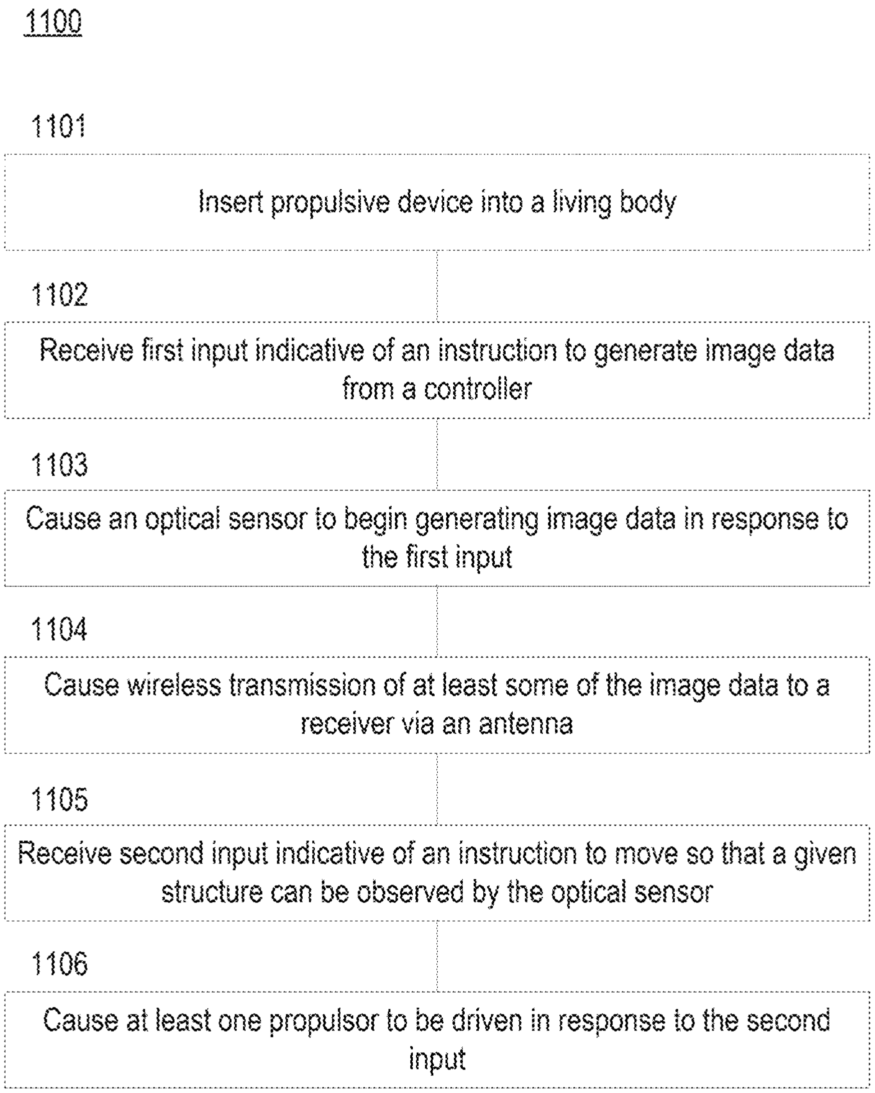
FIG. 11 depicts a flow diagram of a process for controlling a propulsive ingestible device that has an optical sensor as it travels through a living body.

FIG. 11 depicts a flow diagram of a process 1100 for controlling an ingestible device that has an optical sensor as it travels through a living body. Initially, the ingestible device is inserted into the living body (step 1101). For example, if the ingestible device is designed to monitor the digestive system, then the ingestible device may be ingested by a subject. As the ingestible device travels through the living body, the ingestible device may receive first input indicative of an instruction to begin recording image data from a controller located outside the living body (step 1102).

The ingestible device may cause the optical sensor to begin generating image data in response to the first input (step 1103). Alternatively, the optical sensor could be configured to automatically begin generating image data after the ingestible device has been removed from its packaging, or after a mechanical switch accessible along the exterior surface of the ingestible device has been activated. In some embodiments, the ingestible device can be remotely activated by a source located outside the living body via RF signals, magnetic signals, optical signals, etc. For example, the optical sensor may begin generating image data responsive to determining that the ingestible device has been outside of the packaging for a certain amount of time (e.g., 3 minutes, 5 minutes, 10 minutes, etc.). As another example, the optical sensor may begin generating image data responsive to determining that the ingestible device has entered a particular in vivo environment.

The ingestible device can then wirelessly transmit at least some of the image data to a receiver using an antenna (step 1104). For example, a processor may transmit the image data to a transceiver responsible for modulating the image data onto the antenna for transmission to the receiver. In some embodiments, the image data is transmitted in its original (i.e., raw) form. In other embodiments, the image data is transmitted in a processed form. For example, the processor may filter values from the image data, add metadata (e.g., specifying a location, time, or identifier associated with the living body), etc. As noted above, the receiver may be part of the controller or some other electronic device. For example, a medical professional may view the image data and control the ingestible device using a mobile workstation that is wirelessly connected to the ingestible device. As another example, a medical professional may view the image data on a tablet computer and control the ingestible device using a dedicated input device that is similar to controllers for video game consoles.

In some instances, the medical professional may wish to view a particular structure in the living body. Accordingly, the ingestible device may receive a second input indicative of an instruction to move so that the structure can be observed by the optical sensor (step 1105). Said another way, the ingestible device may move so that the structure is located in a field of view (FoV) of the optical sensor. The ingestible device may move by altering its position and/or orientation. The ingestible device may determine the appropriate driving signal for each propulsion component based on the desired position and/or characteristics of the in vivo environment, such as viscosity, flow rate, temperature, etc. Once the ingestible device has reached the desired position, the ingestible device may automatically maintain its position until a predetermined interval of time expires or until an instruction to move to a new position is received from the controller.

The ingestible device can then cause at least one propulsor to be driven in response to the second input (step 1106). In some embodiments, the propulsor(s) are driven based entirely on the second input. For example, if the second input is representative of an instruction to move forward, the propulsor(s) can be driven to achieve forward movement.

For embodiments of the ingestible device that are powered using an onboard battery, it is generally desirable to minimize battery discharge before the ingestible device is ready to be used in order to maximize the amount of power available during operation. To avoid battery drain during shipping and storage prior to deployment, the ingestible device may enter a low-power inactive state where current drawn from the battery is minimized or the battery is disconnected from other components (e.g., with a mechanical switch, a transistor such as a MOSFET, or some other means). To leave this state, the ingestible device may be activated by a sensor.

Some embodiments of the ingestible device employ a photosensor that prompts activation when light is detected. The photosensor may be configured to generate readings indicative of the level of visible, infrared, or ultraviolet light that is presently detectable. In these embodiments, the ingestible device may be shipped and stored in a substantially opaque package to prevent the photosensor from being activated inadvertently or prematurely. When the package is opened, the photosensor will be exposed to light and the ingestible device can be activated. Other embodiments of the ingestible device employ a low-power magnetic sensor that activates when the ingestible device is exposed to a magnetic field. Alternatively, the ingestible device may include a low-power magnetic sensor that activates when the ingestible device is not exposed to a magnetic field. For instance, a magnet may be included in the packaging so that the ingestible device is exposed to a magnetic field at all times while being shipped and stored. This embodiment has several advantages. First, there is minimal risk of premature activation since the packaging is likely to accompany the ingestible device until deployment is imminent. Second, the individual responsible for deploying the ingestible device does not need to introduce an activation signal such as a magnetic field. Other embodiments of the ingestible device may use a reed relay as a mechanical power switch to activate the ingestible device upon being exposed to a magnetic field. In embodiments where the ingestible device is activated by exposure to a magnetic field, a single- or multiple-use magnetic fixture could be used to facilitate activation by holding the magnet in the correct orientation with respect to the ingestible device. Other embodiments of the ingestible device may be activated by a mechanical element (e.g., a switch or button) that is sealed to prevent fluid ingress but is located along the exterior surface of the enclosure so as to be accessible.

As discussed above, the ingestible device may have built-in features, such as sensors, software, and the like, for performing self-diagnostic tests. Using these built-in features, health and performance functions of the ingestible device can be regularly tested. These built-in features can also help in debugging and exploring new operational regimes. Examples of self-diagnostic tests include checksum errors, software versioning, battery voltage, power draw per motor, tests of other major components, etc. Alternately or additionally, the camera may be commanded to generate a test image (e.g., of packaging) to be transmitted to a destination (e.g., the controller), where it may be compared to an expected reference image. Successful transmission of the test image would require the ingestible device be functioning properly. If the test image is not received or is not correct, it could signify a defect (e.g., in the ingestible device, communication channel, etc.) for which an alert may be generated that indicates that the ingestible device should not be deployed.

Communication Environment

Figure 12:
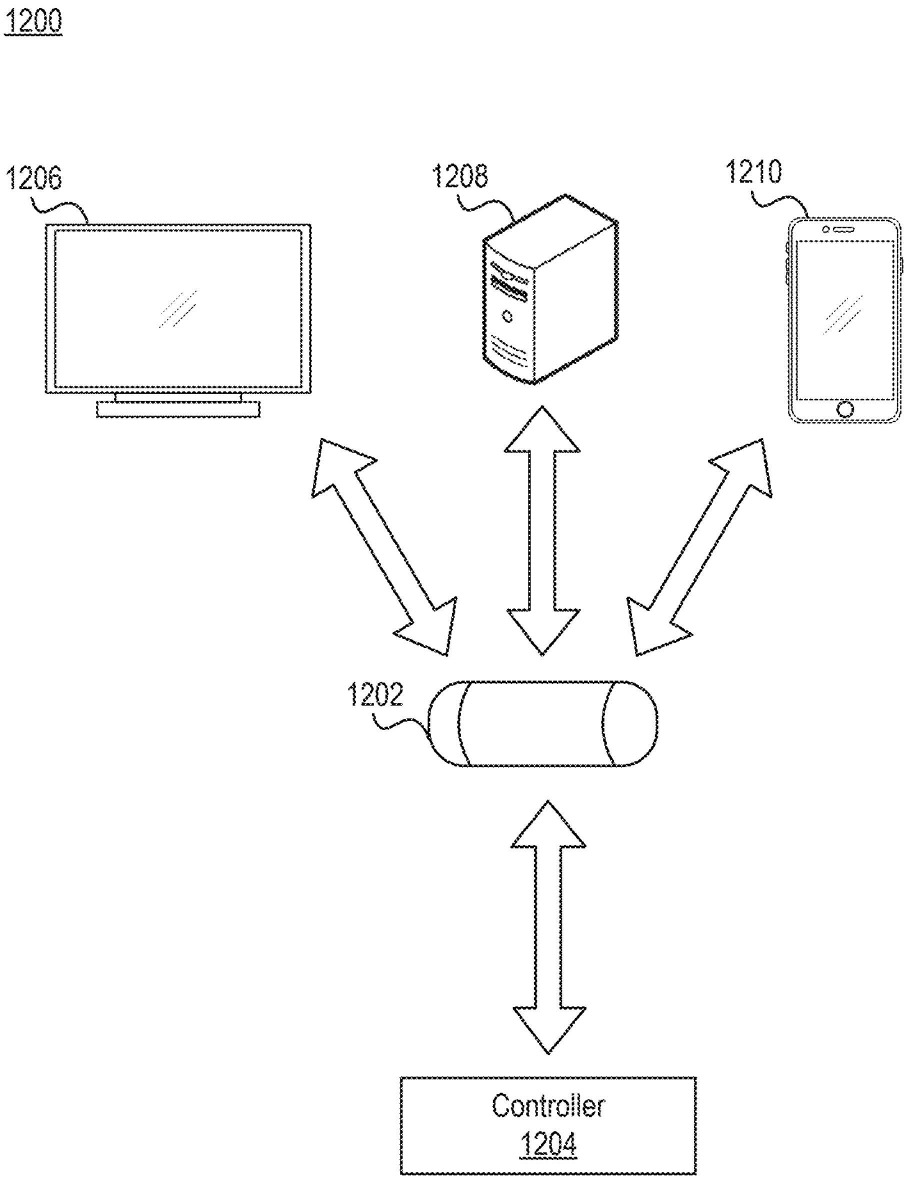
FIG. 12 depicts an example of a communication environment that includes a propulsive ingestible device that is communicatively coupled to a controller.

FIG. 12 depicts an example of a communication environment 1200 that includes an ingestible device 1202 that is communicatively coupled to a controller 1204. An operator can control the ingestible device 1202 using the controller 1204. Moreover, the ingestible device 1202 can be configured to transmit data (e.g., image data or biometric data) to one or more electronic devices. Examples of electronic devices include monitors 1206, computer servers 1208, and mobile phones 1210. The ingestible device 1202, controller 1204, and electronic device(s) may collectively be referred to as the "networked devices."

In some embodiments, the networked devices are connected to one another via point-to-point wireless connections as shown in FIG. 12. For example, the ingestible device 1202 may be communicatively coupled to the controller 1204 via Bluetooth®, Near Field Communication (NFC), Wi-Fi® Direct (also referred to as "Wi-Fi P2P"), Zigbee®, another commercial point-to-point protocol, or a proprietary point-to-point protocol. In other embodiments, the networked devices are connected to one another via networks, such as personal area networks (PANs), local area networks (LANs), wide area networks (WANs), metropolitan area networks (MANs), cellular networks, or the Internet. For example, the ingestible device 1202 may be communicatively coupled to a monitor 1206 and a computer server 1208 via separate LoRa® communication channels.

The connections established between the networked devices may be bidirectional or unidirectional. For example, the controller 1204 may be permitted to transmit data to the ingestible device 1202 even though the ingestible device 1202 may be unable to transmit data to the controller 1204. Similarly, the ingestible device 1202 may be permitted to transmit data to the electronic device(s) even though the electronic device(s) may be unable to transmit data to the ingestible device 1202.

Embodiments of the communication environment 1200 may include some or all of the networked devices. For example, some embodiments of the communication environment 1200 include an ingestible device 1202 and a single device (e.g., a mobile phone, tablet computer, or mobile workstation) that serves as the controller and the electronic device on which image data is reviewed. As another example, some embodiments of the communication environment 1200 include an ingestible device 1202 and a computer server 1208 on which the image data is stored for subsequent review. In such embodiments, because the image data will be reviewed at some later point in time, the communication environment 1200 need not include a controller 1204. As another example, some embodiments of the communication environment 1200 include a dedicated input device without display capabilities that serves as the controller 1204 and an electronic device, such as a tablet computer or a mobile phone, on which image data is reviewed. In such embodiments, the dedicated input device may be communicatively coupled to the ingestible device and/or the electronic device.

Since the ingestible device 1202 can operate in vivo, the close proximity to fluids, tissue, and the like may affect the electromagnetic operating characteristics of the antenna. To address this, the antenna may be designed and/or selected to minimize the effects of nearby materials having relative dielectric constants that are significantly different from free space. As an example, an embodiment could use a small loop antenna with one or more turns, which primarily interacts with magnetic field components in the near field, and is therefore less strongly affected by the proximity of high-dielectric materials. Alternatively, the antenna may be designed and/or selected to compensate for the effect of the fluid(s) inside the living body. As an example, an embodiment could use a straight, bent, curved, or meandered antenna (e.g., monopole antenna) where the effective electrical antenna length is between one-eighth and one-third of the transceiver operating wavelength when the ingestible device 1202 is surrounded by fluid or anatomy of the living body. For instance, an embodiment could use a monopole or "whip" antenna that is significantly shorter than a free-space quarter wavelength. While this antenna would not be tuned optimally in air, proximity to the high-dielectric fluid(s) may cause the antenna to behave electrically as if it were significantly longer and tuned properly to the frequency of interest. Such an approach also has the benefit of allowing the use of a significantly smaller antenna than would be optimal for operation in dry air. The mechanical structure of the antenna may be designed to conform to the enclosure of the ingestible device 1202.

The antenna and transceiver circuitry may be designed such that a single antenna is used for both transmitting and receiving data. Alternatively, multiple antennas may be used. For example, different antennas may offer superior performance in certain orientations or fluid conditions, and the performance of each antenna may be monitored during operation in order to select the antenna with the highest performance at any given point in time. In embodiments that use wireless power transmission, the ingestible device 1202 may be configured to use a single antenna for both power and data transmission to eliminate the need for an additional antenna. Alternatively, different antennas or electromagnetically coupled structures may be used for power and data transmission, allowing each to be optimized for its respective task.

To allow multiple ingestible devices to operate within close proximity (e.g., multiple patients undergoing treatment in the same room or building), the communication channels discussed above may be established using a pairing feature. Pairing features may be employed to ensure that each ingestible device communicates with a single controller. To accomplish this, each ingestible device may be assigned a unique identification number during manufacturing. When a communication channel is established by an ingestible device, the ingestible device may transmit its identifier to establish whether the communication channel was established with the appropriate controller. Additionally or alternatively, the ingestible device may append the identifier (or a shortened/amended identifier) as a label to data packets to designate the appropriate controller. Accordingly, each controller may assume that data packets without the correct identifier are meant to be received by another controller and thus can be ignored. As part of this process, the ingestible device and corresponding controller may elect to switch to a different communication channel or frequency to avoid having to share time and bandwidth with other pairs of ingestible devices and controllers. The ingestible device and corresponding controller may elect to change communication frequency as needed during operation to avoid competing with interfering devices, a strategy known as "frequency hopping."

Processing System

Figure 13:
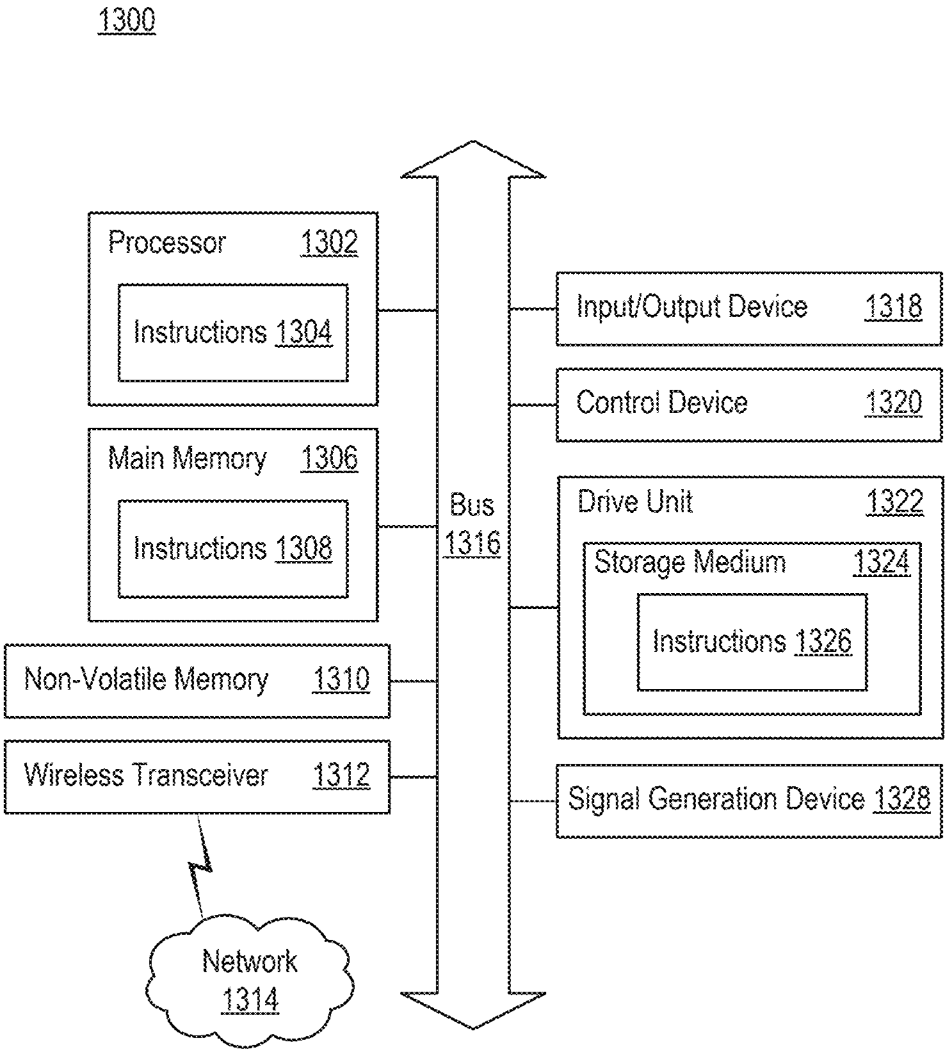
FIG. 13 is a block diagram illustrating an example of a processing system in which at least some operations described herein can be implemented.

FIG. 13 is a block diagram illustrating an example of a processing system 1300 in which at least some operations described herein can be implemented. Components of the processing system 1300 may be hosted on an ingestible device (e.g., ingestible device 100 of FIG. 1).

The processing system 1300 may include a central processing unit ("processor") 1302, main memory 1306, non-volatile memory 1310, wireless transceiver 1312, input/output device 1318, control device 1320, drive unit 1322 including a storage medium 1324, and signal generation device 1328 that are communicatively connected to a bus 1316. The bus 1316 is illustrated as an abstraction that represents one or more physical buses and/or point-to-point connections that are connected by appropriate bridges, adapters, or controllers. The bus 1316, therefore, can include a system bus, Peripheral Component Interconnect (PCI) bus, PCI-Express bus, HyperTransport bus, Industry Standard Architecture (ISA) bus, Small Computer System Interface (SCSI) bus, Universal Serial Bus (USB), Inter-Integrated Circuit ($I^2C$) bus, or bus compliant with Institute of Electrical and Electronics Engineers (IEEE) Standard 1394.

The processing system 1300 may share a similar computer processor architecture as that of a desktop computer, tablet computer, mobile phone, video game console, wearable electronic device (e.g., a watch or fitness tracker), network-connected ("smart") device (e.g., a television or home assistant device), augmented or virtual reality system (e.g., a head-mounted display), or another electronic device capable of executing a set of instructions (sequential or otherwise) that specify action(s) to be taken by the processing system 1300.

While the main memory 1306, non-volatile memory 1310, and storage medium 1324 are shown to be a single medium, the terms "storage medium" and "machine-readable medium" should be taken to include a single medium or multiple media that stores one or more sets of instructions 1326. The terms "storage medium" and "machine-readable medium" should also be taken to include any medium that is capable of storing, encoding, or carrying a set of instructions for execution by the processing system 1300.

In general, the routines executed to implement the embodiments of the disclosure may be implemented as part of an operating system or a specific application, component, program, object, module, or sequence of instructions (collectively referred to as "computer programs"). The computer programs typically comprise instructions (e.g., instructions 1304, 1308, 1326) set at various times in various memories and storage devices in an electronic device. When read and executed by the processor 1302, the instructions cause the processing system 1300 to perform operations to execute various aspects of the present disclosure.

While embodiments have been described in the context of fully functioning electronic devices, those skilled in the art will appreciate that the various embodiments are capable of being distributed as a program product in a variety of forms. The present disclosure applies regardless of the particular type of machine- or computer-readable medium used to actually cause the distribution. Further examples of machine- and computer-readable media include recordable-type media such as volatile and non-volatile memory devices 1310, removable disks, hard disk drives, optical disks (e.g., Compact Disk Read-Only Memory (CD-ROMS) and Digital Versatile Disks (DVDs)), cloud-based storage, and transmission-type media such as digital and analog communication links.

The wireless transceiver 1312 enables the processing system 1300 to mediate data in a network 1314 with an entity that is external to the processing system 1300 through any wireless communication protocol supported by the processing system 1300 and the external entity. The wireless transceiver 1312 can include, for example, an integrated circuit (e.g., enabling communication over Bluetooth or Wi-Fi), network adaptor card, or wireless network interface card.

The techniques introduced here can be implemented using software, firmware, hardware, or a combination of such forms. For example, aspects of the present disclosure may be implemented using special-purpose hardwired (i.e., non-programmable) circuitry in the form of application-specific integrated circuits (ASICs), programmable logic devices (PLDs), field-programmable gate arrays (FPGAs), and the like.

Remarks

The foregoing description of various embodiments has been provided for the purposes of illustration. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes various embodiments, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A method performed by an ingestible device that is designed for ingestion by a living body and that includes a camera and multiple propulsors, the method comprising:

receiving input that is indicative of an instruction, provided via a controller that is external to the living body, to alter a position and/or an orientation of the ingestible device and to stabilize the ingestible device in the altered position and/or orientation;

operating, independently yet simultaneously, the multiple propulsors of the ingestible device based on the input;

causing the camera to capture an image of a biological structure within the living body while the ingestible device is maintained in the altered position and/or orientation as a result of said operating; and forwarding the image to a transceiver for wireless transmission to a destination that is external to the ingestible device.

2. The method of claim 1, further comprising:

examining values that are output by a sensor and that are indicative of measurements of a characteristic of the living body.

3. The method of claim 2, wherein said operating comprises generating a signal for driving the multiple propulsors that is based on the values and varied in real time to account for changes in the values.

4. The method of claim 2, wherein the characteristic is pH.

5. The method of claim 1, wherein the camera is equipped with either a charge-coupled device (CCD) or a complementary metal-oxide-semiconductor (CMOS) sensor that is capable of detecting electromagnetic radiation in a visible range and an infrared sensor that is capable of detecting electromagnetic radiation in an infrared range.

6. The method of claim 1, wherein the ingestible device further includes a sensor that is capable of detecting light, and wherein the method further comprises:

exiting a low-power state by supplying power to at least one additional component in response to a determination that an output of the sensor is indicative of a change in light intensity.

7. The method of claim 6, wherein the at least one additional component includes the camera.

8. The method of claim 6, wherein the sensor is configured to generate values that are indicative of a measured level of visible, infrared, or ultraviolet light.

9. The method of claim 1, wherein the ingestible device further includes a sensor that is capable of detecting magnetic fields, and wherein the method further comprises:

exiting a low-power state by supplying power to at least one additional component in response to a determination that an output of the sensor is indicative of a change in magnetic field strength.

10. A method performed by an ingestible device that is designed for ingestion by a living body and that includes multiple propulsors, the method comprising:

receiving input that is indicative of an instruction, provided via a controller that is external to the living body, to position the ingestible device in a given position;

in response to said receiving, generating a signal for operating the multiple propulsors of the ingestible device such that the ingestible device is positioned in the given position, wherein one or more propulsors of the multiple propulsors are arranged in a cross-type configuration such that the one or more propulsors are radially opposite to each other relative to a central axis of the ingestible device; and manipulating the signal, as necessary, to maintain the given position until either a predetermined interval of time expires or another instruction is received from the controller, wherein manipulating the signal causes (i) a first propulsor of the one or more radially opposite propulsors to generate thrust in a first direction and (ii) a second propulsor of the one or more radially opposite propulsors to generate thrust in a second direction that is opposite to the first direction, such that the ingestible device maintains the given position.

11. The method of claim 10, wherein each of the multiple propulsors is independently operated using a different one of multiple signals but the multiple propulsors are operated in conjunction to maintain the given position.

12. The method of claim 10, wherein the ingestible device further comprises an optical sensor, and wherein the method further comprises:

causing the optical sensor to generate image data in response to a determination that a criterion has been met.

13. The method of claim 12, wherein the criterion is entry into a particular in vivo environment.

14. The method of claim 13, wherein the determination whether the ingestible device has entered the particular in vivo environment is based on an analysis of an output of a biometric sensor.

15. The method of claim 12, further comprising:

forwarding, in real time, the image data to a transceiver for wireless transmission to a destination that is external to the ingestible device.

16. The method of claim 12, further comprising:

forwarding, on a periodic basis, the image data generated over a length of time to a transceiver for wireless transmission to a destination that is external to the ingestible device.

17. The method of claim 16, wherein the length of time is at least 60 seconds.

18. A device that is designed for ingestion by a living body, the device comprising:

multiple propulsors;

a camera; and a processor that is configured to— receive input that is indicative of an instruction, provided via a controller that is external to the living body, to alter a position of the device within the living body and to stabilize the device in the altered position;

operate the multiple propulsors based on the input; and cause the camera to capture an image of a biological structure within the living body while the device is stabilized in the altered position.

19. The method of claim 10, wherein the one or more propulsors that are radially opposite each other relative to the central axis share a common chirality while second one or more propulsors of the multiple propulsors that are rotationally adjacent each other relative to the central axis have opposite chirality.

20. The device of claim 18, wherein the multiple propulsors are arranged in a cross-type configuration such that propulsors that are radially opposite each other relative to a central axis share a common chirality while propulsors that are rotationally adjacent each other relative to the central axis have opposite chirality.

* * * * *